(12) United States Patent
Shimizu et al.

(10) Patent No.: US 8,353,816 B2
(45) Date of Patent: Jan. 15, 2013

(54) ENDOSCOPY SYSTEM AND METHOD THEREFOR

(75) Inventors: Kunimasa Shimizu, Minato-ku (JP); Kenichi Otani, Ashigarakami-gun (JP); Naoto Kinjo, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 952 days.

(21) Appl. No.: 12/397,409

(22) Filed: Mar. 4, 2009

(65) Prior Publication Data
US 2009/0227837 A1 Sep. 10, 2009

(30) Foreign Application Priority Data
Mar. 10, 2008 (JP) ................................. 2008-059543

(51) Int. Cl.
*A61B 1/04* (2006.01)
*A61B 1/00* (2006.01)
(52) U.S. Cl. ........ 600/113; 600/103; 600/109; 600/117; 348/65; 348/72; 348/74; 382/128
(58) Field of Classification Search .................. 600/103, 600/109, 113, 117, 160, 178, 180; 348/65, 348/72, 74; 382/128
See application file for complete search history.

(56) References Cited

U.S. PATENT DOCUMENTS

| | | | |
|---|---|---|---|
| 5,436,655 A * | 7/1995 | Hiyama et al. ................... | 348/45 |
| 2003/0032878 A1 * | 2/2003 | Shahidi .......................... | 600/429 |
| 2003/0135091 A1 * | 7/2003 | Nakazawa et al. ............. | 600/113 |
| 2003/0144585 A1 * | 7/2003 | Kaufman et al. .............. | 600/407 |
| 2005/0107666 A1 * | 5/2005 | Glukhovsky et al. .......... | 600/117 |
| 2005/0165272 A1 * | 7/2005 | Okada et al. ................... | 600/114 |
| 2005/0256402 A1 * | 11/2005 | Kawashima et al. .......... | 600/437 |
| 2006/0235273 A1 * | 10/2006 | Moriyama et al. ............ | 600/113 |
| 2007/0001879 A1 * | 1/2007 | Kaftan et al. ................... | 341/79 |
| 2007/0049803 A1 * | 3/2007 | Moriyama ..................... | 600/176 |
| 2007/0055128 A1 * | 3/2007 | Glossop ......................... | 600/407 |

(Continued)

FOREIGN PATENT DOCUMENTS

JP 63-242233 A 10/1988

(Continued)

OTHER PUBLICATIONS

Notification of Reasons for Refusal, dated Jul. 11, 2012, issued in corresponding JP Application No. 2008-059543, 6 pages in English and Japanese.

*Primary Examiner* — John P Leubecker
*Assistant Examiner* — Arnaldo Torres Diaz
(74) *Attorney, Agent, or Firm* — Sughrue Mion, PLLC

(57) ABSTRACT

A capsule endoscope is swallowed by a patient, to capture images from inner wall surfaces of patient's digestive tract, while detecting imaging positions of the capsule endoscope. A doctor observes the images captured by the capsule endoscope, to select an aimed point image that contains a portion suspected of a lesion, and some images that represent pass points on an insertion route of a balloon endoscope. While a probing tip of the balloon endoscope is being inserted into the patient for the sake of thorough examination of the suspected portion, a degree of similarity between an image captured by the balloon endoscope and an image of a destination point, which is one of the pass points and the aimed point, is detected to judge by the similarity whether the probing tip has reached the destination point or not. So the doctor can get the probing tip to the aimed point easily.

12 Claims, 18 Drawing Sheets

U.S. PATENT DOCUMENTS

| | | | |
|---|---|---|---|
| 2007/0142705 A1* | 6/2007 | Ohnishi et al. | 600/109 |
| 2007/0161855 A1* | 7/2007 | Mikkaichi et al. | 600/113 |
| 2007/0255100 A1* | 11/2007 | Barlow et al. | 600/114 |
| 2008/0004529 A1* | 1/2008 | Kawashima et al. | 600/443 |
| 2008/0024599 A1* | 1/2008 | Hirakawa | 348/65 |
| 2008/0071140 A1* | 3/2008 | Gattani et al. | 600/117 |
| 2008/0095418 A1* | 4/2008 | Moriya | 382/128 |
| 2008/0097155 A1* | 4/2008 | Gattani et al. | 600/117 |
| 2008/0112604 A1* | 5/2008 | Lloyd | 382/131 |
| 2008/0242926 A1* | 10/2008 | Nishino | 600/109 |
| 2009/0036775 A1* | 2/2009 | Ikuma et al. | 600/443 |
| 2009/0051695 A1* | 2/2009 | Matsuda | 345/556 |
| 2009/0060300 A1* | 3/2009 | Neemuchwala et al. | 382/128 |
| 2009/0080742 A1* | 3/2009 | Moriya | 382/131 |
| 2009/0086905 A1* | 4/2009 | Boyden et al. | 378/46 |
| 2009/0253954 A1* | 10/2009 | Katayama | 600/103 |
| 2009/0292175 A1* | 11/2009 | Akimoto et al. | 600/156 |
| 2009/0309961 A1* | 12/2009 | Miyashita | 348/65 |
| 2009/0322863 A1* | 12/2009 | Takahashi | 348/65 |
| 2010/0232661 A1* | 9/2010 | Hisanaga et al. | 382/128 |
| 2011/0075901 A1* | 3/2011 | Nakamura | 382/128 |
| 2012/0130171 A1* | 5/2012 | Barak et al. | 600/117 |

FOREIGN PATENT DOCUMENTS

| | | |
|---|---|---|
| JP | 2003-265405 A | 9/2003 |
| JP | 2005-021516 A | 1/2005 |
| JP | 2005-102851 A | 4/2005 |
| JP | 2005-192880 A | 7/2005 |
| JP | 2005-334331 A | 12/2005 |
| JP | 2006-068109 A | 3/2006 |
| JP | 2006-239053 A | 9/2006 |
| JP | 2007-068763 A | 3/2007 |
| JP | 2007-236700 A | 9/2007 |
| JP | 2007-319442 A | 12/2007 |

* cited by examiner

|  | D=vR−vL | |
|---|---|---|
|  | CONVEX | CONCAVE |
| P1 | D>0 | D<0 |
| P2 | D≒0 | D≒0 |
| P3 | D<0 | D>0 |
| vR:LUMINANCE UNDER LIGHT FROM FIRST LIGHT SOURCE vL:LUMINANCE UNDER LIGHT FROM SECOND LIGHT SOURCE | | |

US 8,353,816 B2

ENDOSCOPY SYSTEM AND METHOD THEREFOR

FIELD OF THE INVENTION

The present invention relates to an endoscopy system and a method for the endoscopy system, wherein a capsule endoscope is used for a primary examination and a flexible endoscope is used to capture images from those body sites which are determined to need a thorough examination as a result of the primary examination.

BACKGROUND OF THE INVENTION

Endoscopy with a capsule endoscope has recently been put into practical use. The capsule endoscope has its components, including an imaging device and a light source, integrated in a micro capsule. A patient first swallows the capsule endoscope so that the imaging device captures images from internal body sites, i.e. internal surfaces of patient's tracts, while the light source is illuminating those sites. Image data captured by the imaging device is transmitted as a radio signal to a receiver that is attached to the patient. The image data is sequentially recorded on a storage medium like a flash memory, which is provided in the receiver.

In parallel to the imaging of the body sites by the capsule endoscope, the position of the capsule endoscope inside the patient is detected. For example, JPA 2005-192880 and JPA 2007-236700 suggest sending out a radio wave from the capsule endoscope and detecting the strength of the radio wave received on an antenna, which may be mounted on a shielding shirt or the like that the patient wears. Then data on the position of the capsule endoscope is derived from the strength of the received electric wave, and is recorded in association with the image data of the inspected sites on the storage medium.

To complete the endoscopy with the capsule endoscope, the receiver is connected to an information managing apparatus like a workstation via an USB cable or the like, so that the whole image data stored in the receiver is taken into the information managing apparatus. On the basis of the image data taken into the information managing apparatus, a doctor has the captured images displayed on a monitor to interpret them. When the doctor finds any suspected part, i.e. such a part that looks like a lesion, in some images, the doctor takes images from the suspected part with a flexible endoscope like a balloon endoscope, to make a complete examination.

If the suspected part is found in those images taken from inside a small intestine, a probing tip of the balloon endoscope is inserted into the small intestine to take images of an aimed point by an imaging device that is built in the probing tip. The aimed point is where the suspected part may exit, and its position is located in advance on the basis of the position data of the capsule endoscope that is recorded in association with the image data of the suspected part. Image signals from the imaging device are sent to a processor that is connected to the balloon endoscope. Then the processor processes the image signals to display an endoscopic image on a monitor, so that the doctor interprets the displayed image for diagnosis.

To insert the probing tip of the balloon endoscope into the small intestine to reach the aimed point, the small intestines are drawn in with a balloon that is provided on the probing tip. As a result, the doctor tends to lose track of the aimed point because the aimed point in the drawn small intestines does not coincide with one indicated by the position data that was detected by the capsule endoscope in the normal condition of the small intestines. So it takes a pretty long time to search for the aimed point, which elongates the total time taken for the endoscopy and thus increases the load on the patient.

SUMMARY OF THE INVENTION

In view of the foregoing, a primary object of the present invention is to provide an endoscopy system and an endoscopy method, which make it possible to detect a relative position of a probing tip of a flexible endoscope such as a balloon endoscope inside a test body while the probing tip is being inserted into the test body, on the assumption that the endoscopy system and the endoscopy method use a capsule endoscope swallowed by a test body to capture first kind of images from internal portions of the test body and a flexible endoscope having a flexible inserter with an imaging device, which is inserted in the test body to capture second kind of images by the imaging device when the doctor finds it necessary to make a thorough examination of an aimed point inside the test body as a result of interpretation of the first kind of images.

The endoscopy system of the present invention comprises an aimed point selection device for selecting an aimed point image that contains the aimed point from among the first kind of images in response to an operation by the doctor; a similarity detection device for detecting similarity between the aimed point image and the second kind of images as captured by the imaging device while the flexible inserter is being moved toward the aimed point; a position information obtaining device for obtaining information on a relative position of the imaging device of the flexible endoscope inside the test body on the basis of the similarity detected by the similarity detection device; and a display device for displaying the information on the relative position of the imaging device inside the test body.

According to a preferred embodiment, the endoscopy system further comprises a pass point selection device for selecting at least a pass point image from among the first kind of images, the pass point image being representative of a pass point on a route from an inlet of the flexible inserter to the aimed point, wherein the similarity detection device further detects similarity between the pass point image and the second kind of images while the flexible inserter is being inserted into the test body, and the position information obtaining device obtains the information on the relative position of the imaging device to the pass point or to the aimed point on the basis of the similarity between the pass point image and the second kind of images or the similarity between the aimed point image and the second kind of images, respectively.

Preferably, the display device displays information as to whether the imaging device has reached the pass point and the aimed point as the information on the relative position of the imaging device.

Preferably, the similarity detection device detects the similarity between the pass point image and the second kind of images by calculation using image characteristic values of the pass point image and the second kind of image, and the similarity between the aimed point image and the second kind of images by calculation using image characteristic values of the aimed point image and the second kind of image.

According to a preferred embodiment, the endoscopy system further comprises a first spectral image producing device for producing spectral images of appropriately selected spectral frequency bands from the aimed point image and the pass point image respectively; and a second spectral image producing device for producing a spectral image from each of the second kind of images so that the spectral image has the same spectral frequency band as the spectral image of the pass point has while the imaging device of the inserter is moving toward the pass point, and that the spectral image has the same spectral frequency band as the spectral image of the aimed point has while the imaging device of the inserter is moving from the pass point toward the aimed point, wherein the first image characteristic value taking device takes the image characteristic values from the spectral images of the aimed point and the pass point, whereas the second image characteristic value taking device takes the image characteristic values respectively from the spectral images of the second kind of images.

Preferably, the image characteristic values taken by the first and second image characteristic value taking devices represent blood vessel patterns in the internal portions of the test body.

According to another preferred embodiment, surface asperities of the internal portions of the test body are detected as the image characteristic values. In that case, the capsule endoscope preferably comprises a number of light sources, which are disposed at different positions and sequentially emit light to illuminate the same portion inside the test body. The capsule endoscope captures a corresponding number of images to the number of light sources from the same portion synchronously with the sequential emissions of the light sources toward the same portion. Then, the first image characteristic value taking device estimates the surface asperities of the pass point and the aimed point on the basis of images captured from the pass point and images captured from the aimed point respectively. On the other hand, the inserter of the flexible endoscope is provided with a plurality of illumination windows on different sides of the imaging device, to project illumination light sequentially from one illumination window after another toward the same portion inside the test body, and the imaging device of the flexible endoscope captures a corresponding number of images to the illumination windows from the same portion synchronously with the sequential projection of illumination light from the illumination windows toward the same portion. Then, the second image characteristic value taking device estimates the surface asperities of the same portion on the basis of the images captured by the imaging device of the flexible endoscope from the same portion.

An endoscopy method of the present invention comprises steps of selecting an aimed point image that contains the aimed point from among the first kind of images before inserting the flexible inserter into the test body; detecting similarity between the aimed point image and the second kind of images as captured by the imaging device while the flexible inserter is being moved toward the aimed point; obtaining information on a relative position of the imaging device of the flexible endoscope inside the test body on the basis of the similarity between the aimed point image and the second kind of images; and displaying the obtained information on the relative position of the imaging device.

According to the present invention, information on the relative position of the imaging device of the flexible endoscope inside the test body is obtained on the basis of similarity between the aimed point image that is selected from among the first kind of images as captured by the capsule endoscope, and the second kind of images as captured by the flexible endoscope. Therefore, even while the relative position of the aimed point inside the test body varies during the endoscopy with the flexible endoscope from the relative position of the aimed point during the endoscopy with the capsule endoscope, the present invention ensures detecting whether the imaging device of the flexible endoscope has reached the aimed point or not. As a result, the doctor can get the imaging device of the flexible endoscope to the aimed point in a shorter time than conventional, which contributes to shortening the total time of inspection and thus reducing the load on the patient.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
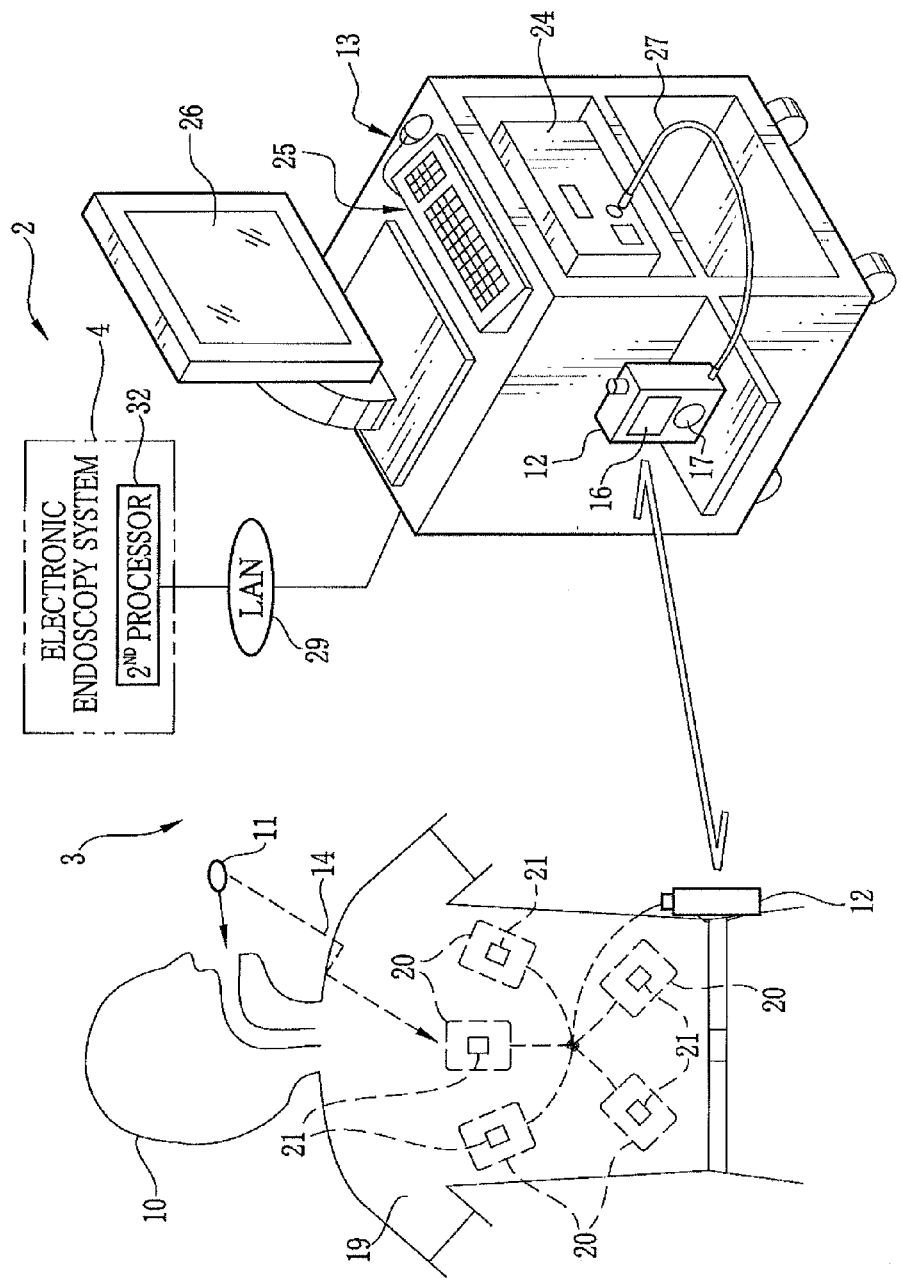
FIG. 1 is a schematic diagram illustrating a capsule endoscopy system as a component of an endoscopy system according to an embodiment of the present invention.
Figure 2:
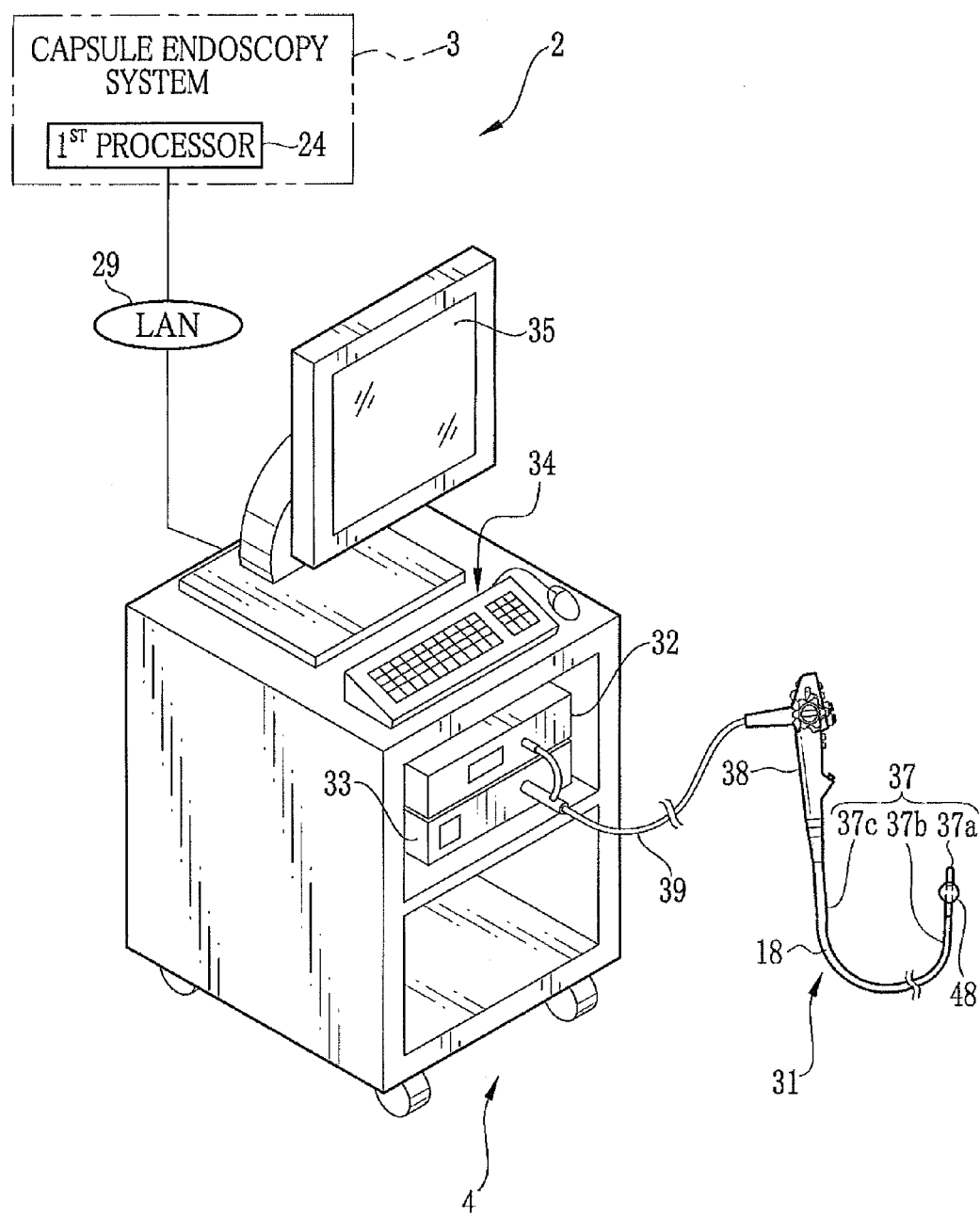
FIG. 2 is a schematic diagram illustrating an electronic endoscopy system as another component of the endoscopy system.

As shown in FIGS. 1 and 2, an endoscopy system 2 consists of a capsule endoscopy system 3 and an electronic endoscopy system 4. In the endoscopy system 2, an endoscopy of a patient or test body 10 is first made using the capsule endoscopy system 3 and, if any suspected part that can be a lesion or the like is found, a thorough examination of the suspected part is made using the electronic endoscopy system 4.

The capsule endoscopy system 3 consists of a capsule endoscope 11 that is swallowed into the patient 10, a portable receiver 12 carried about by the patient 10, and a workstation 13 that takes up images as captured by the capsule endoscope 11 and displays the images for a doctor to interpret them.

The capsule endoscope 11 captures images from internal walls of tracts, e.g. small bowels, of the patient 10, to send data of the captured images to the receiver 12 sequentially as a radio wave 14. The receiver 12 is provided with a liquid crystal display (LCD) 16 for displaying various setup screens and an operating section 17 for setting up the receiver 12 on the setup screens. The receiver 12 receives and stores the image data as transmitted from the capsule endoscope 11 on the radio wave 14, which will be referred to as the CE image data hereinafter.

Figure 3:
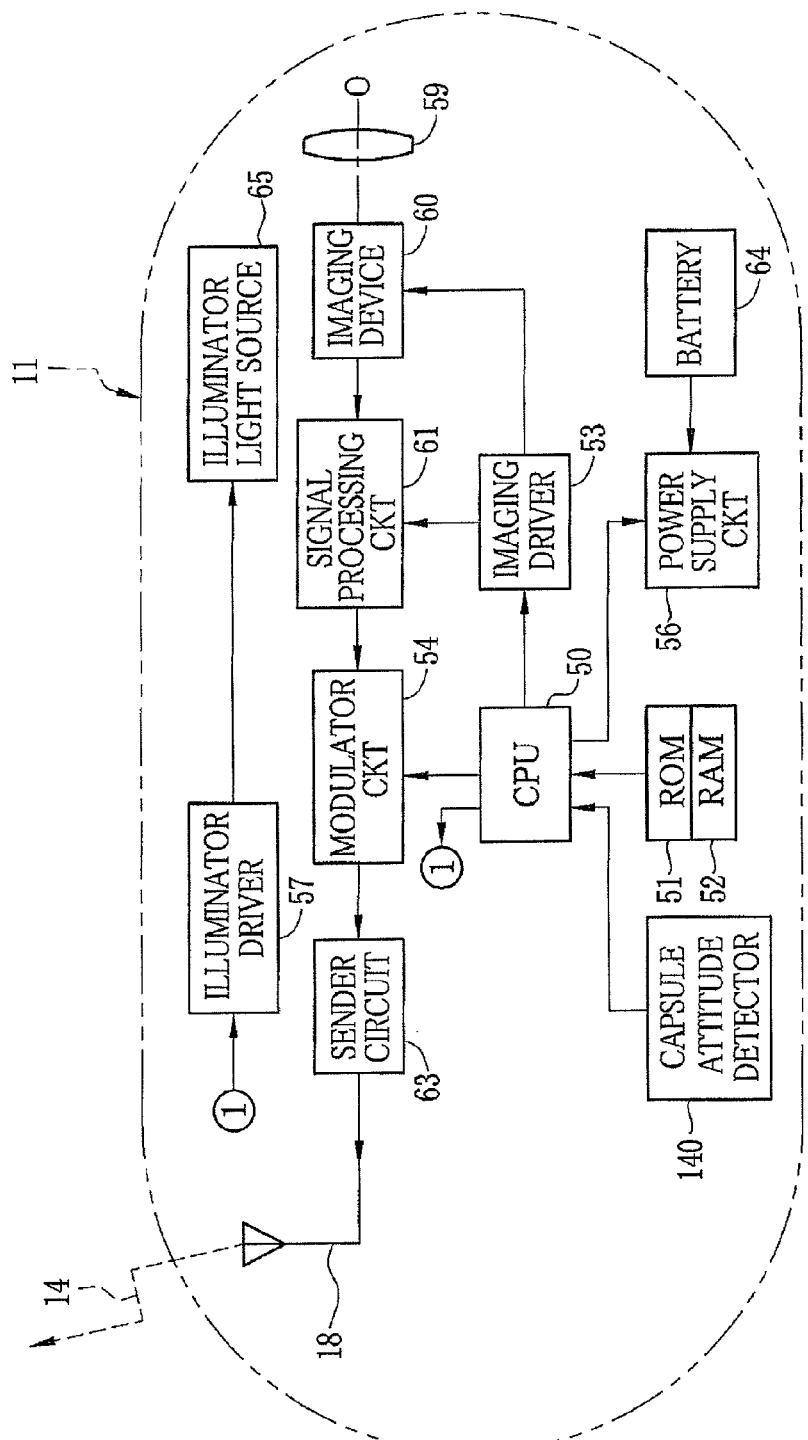
FIG. 3 is a block diagram illustrating an electric structure of the capsule endoscopy system.

The transmission of the radio wave 14 between the capsule endoscope 11 and the receiver 12 is carried out by way of antennas 18 and 20, wherein the antenna 18 is mounted in the capsule endoscope 11, as shown in FIG. 3, whereas the antennas 20 are mounted on a shield shirt 19 that the patient 10 wears. Each of the antennas 20 has an electric field strength sensor 21 built therein for measuring the field strength of the radio wave 14 from the capsule endoscope 11.

The workstation 13 is provided with a first processor 24, operating members 25, including a keyboard and a mouse, and an LCD 26. The first processor 24 is connected to the receiver 12, for example, through an USB cable 27, to exchange data. The first processor 24 may be connected to the receiver 12 through wireless communication like infrared communication. The first processor 24 takes up the CE image data from the receiver 12 during the capsule endoscopy with the capsule endoscope 11 or at the end of the capsule endoscopy, to accumulate and manage the CE image data individually for each patient. Simultaneously, the first processor 24 generates an endoscopic image based on the CE image data, which corresponds to the first endoscopic image as specified above in the summary of the invention, and will be referred to as a CE image hereinafter. The first processor 24 displays the CE image on the LCD 26, so a doctor interprets the CE images on the LCD 26.

The first processor 24 is also connected to a second processor 32 of the electronic endoscopy system 4 through a LAN 29. When the doctor selects some CE images by operating the operating members 25 of the first processor 24, the first processor 24 extracts image characteristic values from the image data of the selected CE images and transmits the extracted characteristic values to the second processor 32 through the LAN 29.

In an embodiment shown in FIG. 2, the electronic endoscopy system 4 is a flexible endoscope for small-bowel examination, which consists of a balloon endoscope 31 that is inserted into the patient 10 through its mouth or another inlet, the second processor 32, an illuminator 33, operating members 34, including a keyboard and a mouse, and an LCD 35. The balloon endoscope 31 is provided with a flexible inserter 37 that is inserted into the patient's body, a handle 38 joined to a base end of the inserter 37, and a universal cord 39 that is connected to the second processor 32 and the illuminator 33.

Figure 9:
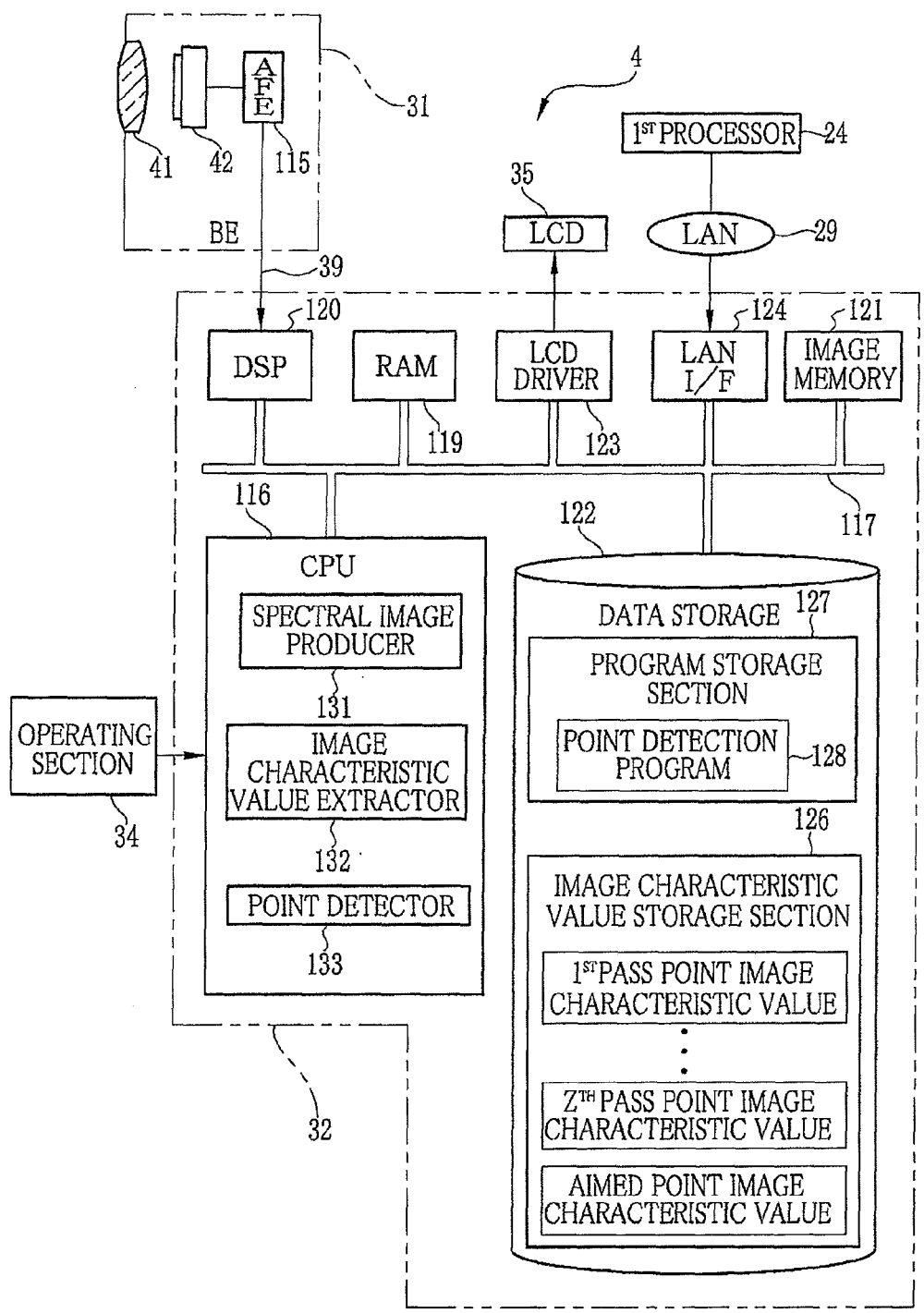
FIG. 9 is a block diagram illustrating an electric structure of a second processor as a component of the electronic endoscopy system.

A probing tip 37a is joined to a distal end of the inserter 37. As shown in FIG. 9, an objective lens 41 and an imaging device 42 are mounted in the probing tip 37a, for capturing images from the internal walls of the patient's tracts, i.e. the small bowels in this embodiment. Analog image signals output from the imaging device 42 are converted to digital image data, hereinafter referred to as the BE image data, and fed to the second processor 32 through the universal cord 39. Simultaneously, illumination light from the illuminator 33 is conducted through an optical fiber cable or the like, which is mounted in the inserter 37, to the probing tip 37a and is projected from the probing tip 37a toward the small bowel internal wall.

A bendable portion 37b is provided behind the probing tip 37a. The bendable portion 37b consists of a number of segments coupled to one another in such a manner that the bendable portion 37b bends in any directions as an angle knob of the handle 38 being operated to push and pull wires that are mounted in the inserter 37. Thereby, the doctor can orient the probing tip 37a to any desirable direction inside the test body by operating the angle knob. Behind the bendable portion 37b is provided a flexible soft portion 37c.

A balloon 48 is mounted between the probing tip 37a and the bendable portion 37b. The balloon 48 is made of an elastically expandable material, e.g. latex rubber. A not-shown ventilator feeds air into and out of the balloon 48 through a not-shown ventilation tube that is provided along inside the inserter 37 and the universal cord 39, causing the balloon 48 to swell out and deflate. As known in the art, the probing tip 37a advances into small bowels by drawing the small bowels with the pinch-and-swell movement of the balloon 48, to perform small-bowel endoscopy with the balloon endoscope 31.

The second processor 32 produces an endoscopic image on the basis of the BE image data from the balloon endoscope 31, and displays the endoscopic image on the LCD 35. Hereinafter the endoscopic image produced based on the BE image data will be referred to as the BE image, which corresponds to the second endoscopic image as specified above in the summary of the invention. Since the BE image is clearer than the CE image, the endoscopy with the balloon endoscope 31 is suitable for detailed examination of a body part under suspicion of a lesion, which was found by the endoscopy with the capsule endoscope 11. The second processor 32 also detects a relative position of the probing tip 37a of the balloon endoscope 31 inside the patient 10 on the basis of the image characteristic values of the CE image data, which are fed from the first processor 24 through the LAN 29, as will be described in detail with reference to FIGS. 10 and 11.

Now the capsule endoscope 11, the receiver 12 and the first processor 24, which constitute the capsule endoscopy system 3, will be described in more detail with reference to FIG. 3. The overall operation of the capsule endoscope 11 is supervised by a CPU 50. The CPU 50 is connected to a ROM 51, a RAM 52, an imaging driver 53, a modulator circuit 54, a power supply circuit 56 and an illuminator driver 57. Designated by a reference numeral 140 in FIG. 3 is an attitude sensor that detects a physical attitude of the capsule endoscope 11 inside the body of the patient 10, which will be described later with respect to a second embodiment.

The CPU 50 reads out necessary programs and data from the ROM 51 and expands them on the RAM 52 to process the read programs sequentially. The imaging driver 53 is connected to an imaging device 60 and a signal processing circuit 61. The imaging device 60 is for example a CCD or a CMOS that captures an image of a subject, a body site or body part, as the image is formed through an objective lens 59. The objective lens 59 has an imaging field of 140 to 180 in front angle of view, and forms an omniazimuth image of the subject existing in the imaging field. The imaging driver 53 controls the operation of the imaging device 60 and the signal processing circuit 61 so as to capture an image at a given frame rate and a shutter speed. Designated by a reference numeral O is an optical axis of the objective lens 59.

The signal processing circuit 61 processes the image signal, which is output from the imaging device 60, through correlated-double sampling, amplification and analog-to-digital conversion, to convert it to the digital CE image data. The signal processing circuit 61 also subjects the CE image data to gamma correction and other image processing processes.

The modulator circuit 54 is connected to an output of the signal processing circuit 61, and an input of a sender circuit 63, which is connected to the antenna 18. The modulator circuit 54 modulates a radio wave in accordance with the CE image data from the signal processing circuit 61, and output the modulated radio wave 14 to the sender circuit 63. The sender circuit 63 outputs the radio wave 14 to the balloon endoscope 18 after amplifying and band-pass filtering it. Thus, the CE image data is transmitted from the capsule endoscope 11 to the receiver 12 wirelessly.

The power supply circuit 56 supplies power from a battery 64 to respective components of the capsule endoscope 11. The illuminator driver 57 drives an illuminator 65 under the control of the CPU 50 so as to illuminate the subject or target body site at a given light volume during the imaging.

Figure 4:
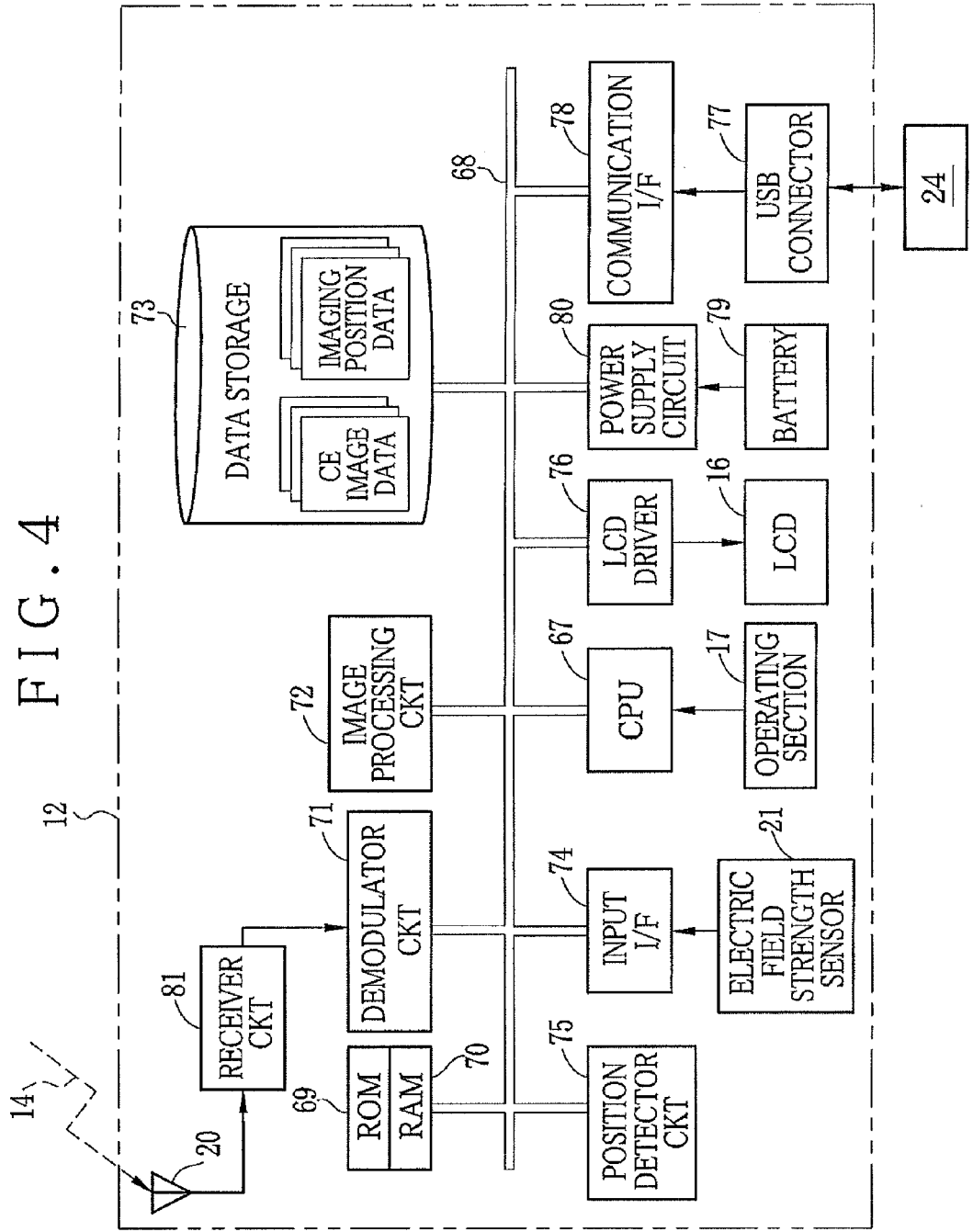
FIG. 4 is a block diagram illustrating an electric structure of a receiver.

As shown in FIG. 4, the overall operation of the receiver 12 is controlled by a CPU 67. A data bus 68 connects the CPU 67 to respective components of the receiver 12, including a ROM 69, a RAM 70, a demodulator circuit 71, an image processing circuit 72, a data storage 73, an input interface (I/F) 74 and a position detector circuit 75. The data bus 68 is also connected to an LCD driver 76 for driving the LCD 16, a communication interface (I/F) 78 for intermediating data exchange between the receiver 12 and the first processor 24 via a USB connector 77, and a power supply circuit 80 for supplying power from a battery 79 to the respective components of the receiver 12.

The CPU 67 reads necessary programs and data from the ROM 69 and expands them on the RAM 70 to process the read programs sequentially. The CPU 67 also controls the respective components of the receiver 12 to work in accordance with operational signals input through the operating section 17. The demodulator circuit 71 is connected to an output of a receiver circuit 81, and an input of the receiver circuit 81 is connected to the antenna 20. The demodulator circuit 71 demodulates the radio wave 14 as received from the capsule endoscope 11 to be the original CE image data, and outputs the CE image data to the image processing circuit 72. The receiver circuit 81 outputs the radio wave 14 as received on the antenna 20 after amplifying and band-pass filtering it.

The image processing circuit 72 processes the CE image data as decoded by the demodulator circuit 71, and outputs the processed CE image data to the data storage 73 while attaching ID information such as a file name to each individual image file of the CE image data. The data storage 73 is for example a flash memory with a memory capacity of about 1 GB. The data storage 73 stores the CE image data as output from the image processing circuit 72. The input interface 74 gets a result of measurement from the electric field strength sensor 21, and outputs the result to the position detector circuit 75.

The position detector circuit 75 detects a present position of the capsule endoscope 11 inside the test body on the basis of the field strength of the radio wave 14 that is measured by the electric field strength sensor 21, and the position detector circuit 75 outputs information on the detected position of the capsule endoscope 11, hereinafter referred to as imaging position data, to the data storage 73. The data storage 73 records the imaging position data in association with the CE image data that is obtained through the capsule endoscope 11 at the imaging position represented by the imaging position data. Since the method of detecting the position of the capsule endoscope 11 inside the test body on the basis of the field strength of the radio wave 14 from the capsule endoscope 11 is well known in the art, details of this method are omitted from the present description.

Figure 5:
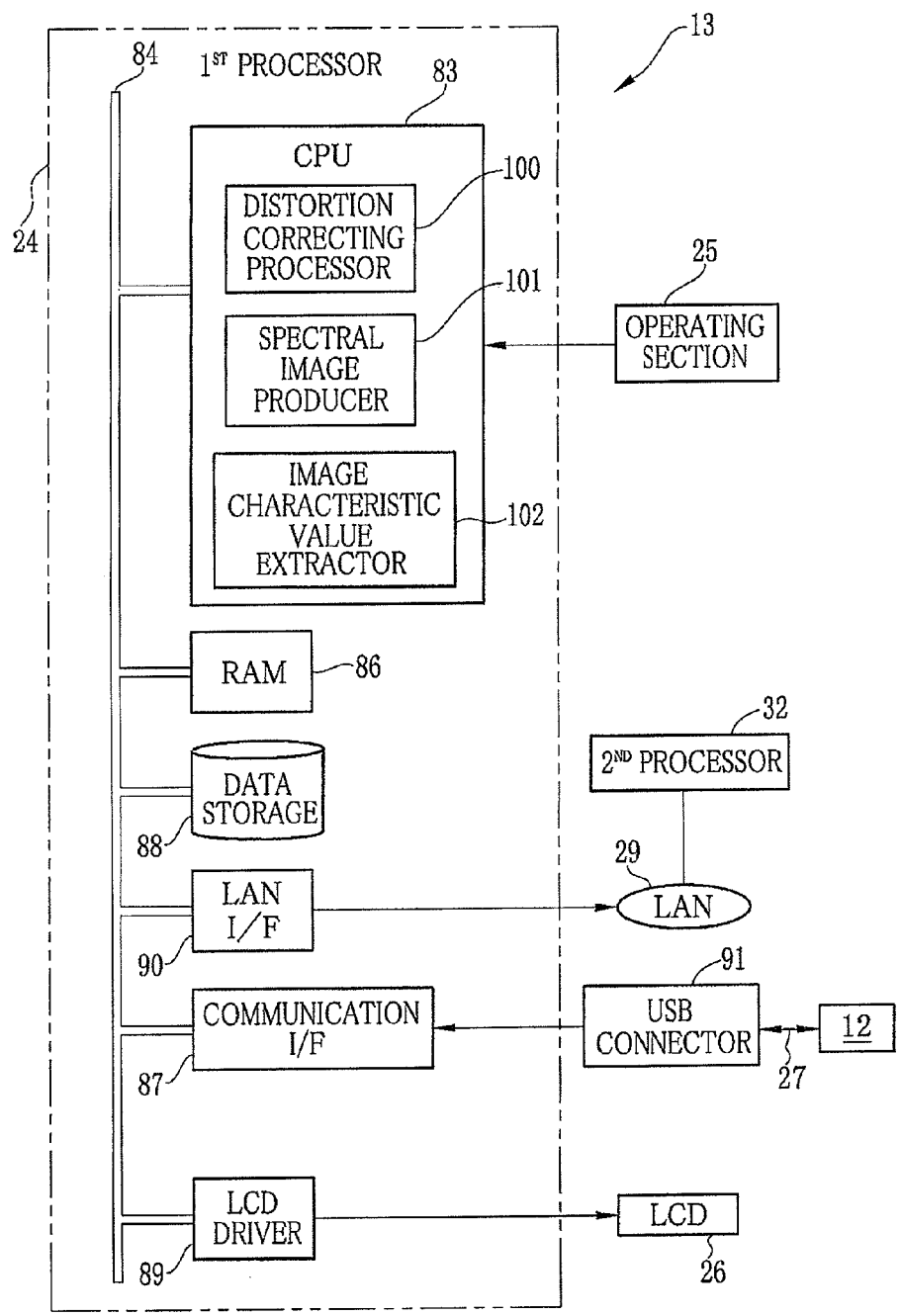
FIG. 5 is a block diagram illustrating an electric structure of a first processor as a component of the capsule endoscopy system.

As shown in FIG. 5, the first processor 24 of the workstation 13 includes a CPU 83 that supervises the overall operation of the workstation 13. A data bus 84 connects the CPU 83 to a RAM 86, a communication interface (I/F) 87 and a data storage 88. The data bus 84 is connected to an LCD driver 89 for driving the LCD 26 and to a LAN interface (I/F) 90 that is connected to the LAN 29.

The CPU 83 reads necessary programs and data out of the data storage 88 and expands them on the RAM 86 to process the read programs sequentially. The CPU 83 also controls the respective components of the workstation 13 to work in accordance with operational signals input through the operating members 25. The communication interface 87 intermediates data exchange between the workstation 13 and the receiver 12 through a USB connector 91, and receives the CE image data and the imaging position data from the receiver 12. The received CE image data and imaging position data are stored in the data storage 88.

Figure 6:
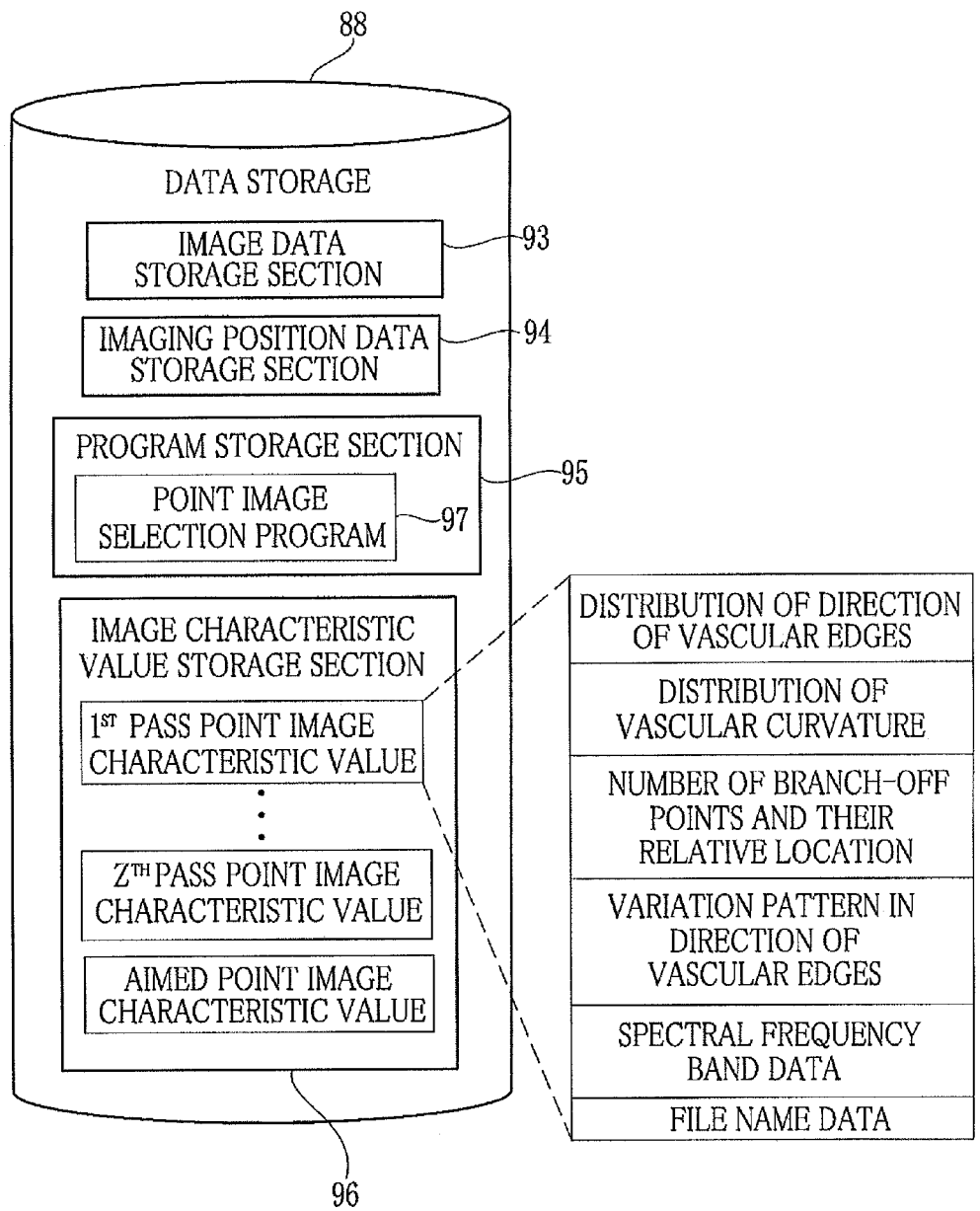
FIG. 6 is an explanatory diagram illustrating data stored in a data storage of the first processor.

As shown in FIG. 6, the data storage 88 has an image data storage section 93, an imaging position data storage section 94, a program storage section 95 and an image characteristic value storage section 96. The image data storage section and the imaging position data storage section 94 store the CE image data and the imaging position data respectively while sorting out the data for one patient from another.

The program storage section 95 stores a point image selection program 97 beside various programs and data for controlling the operation of the first processor 24. When the point image selection program 97 is activated, a point image selection screen 98 (see FIG. 8) is displayed on the LCD 26, allowing selecting images from among those images which correspond to the CE image data fed through the receiver 12.

Figure 7:
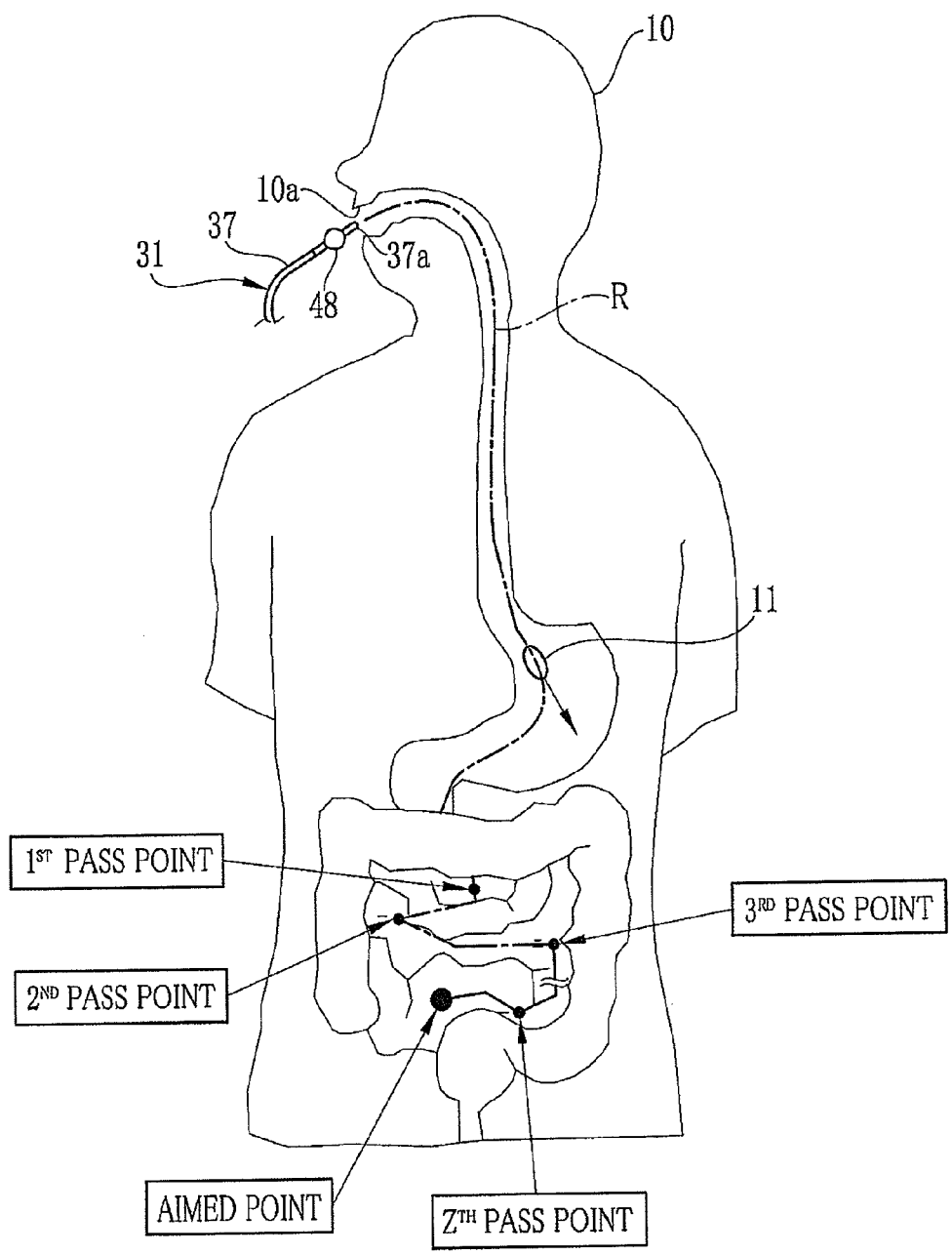
FIG. 7 is an explanatory diagram illustrating an aimed point and pass points on an endoscope insertion route, which are selected by a doctor with reference to images captured by a capsule endoscope.

As shown for example in FIG. 7, if a doctor finds a CE image containing such a questionable portion that can be a lesion as a result of the image interpretation on the LCD 26, the doctor selects the CE image containing the questionable portion as a CE image of an aimed point. Thereafter, the doctor selects at least a second CE image that was taken on the way from an inserting position of the capsule endoscope 11 into the patient 10 to the aimed point. In the example shown in FIG. 7, both the capsule endoscope 11 and the balloon endoscope 31 are inserted through the mouth 10a into the digestive tract of the patient 10, and intermediate points along a route R of insertion of the balloon endoscope 31, which corresponds to the course of movement of the capsule endoscope 11 in this embodiment, are selected serially as first to $Z^{th}$ pass points (Z is an integer larger than 1). Although the present embodiment will be described on the assumption that the aimed point and the pass points are located in the small intestines, these points can be located in any positions inside the test body.

The probing tip 37a of the balloon endoscope 31 enters through the mouth 10a and reaches the aimed point through the first to the $Z^{th}$ pass points. In the following description, a CE image of the aimed point will be called an aimed point image, and CE images of the first to $Z^{th}$ pass points will be called first to $Z^{th}$ pass point images respectively.

The aimed point image and the first to $Z^{th}$ pass point images are utilized for detecting which point the probing tip 37a has reached on the way to the aimed point during the endoscopy with the balloon endoscope 31. As described above, the balloon 48 of the balloon endoscope 31 draws the small intestines in, to thrust the inserter 37 of the balloon endoscope 31 through into the small intestines. The BE image data obtained by the balloon endoscope 31 is compared with the CE image data obtained at the respective pass points and the aimed point, to check similarity between them. Based on the similarity between them, it is possible to detect which point the probing tip 37a has reached. Note that the similarity between the BE image data and the CE image data is judged by image characteristic values that are extracted from the respective image data.

Referring back to FIG. 5, a distortion correcting processor (expanded image producing device) 100, a spectral image producer (first spectral image producer) 101 and an image characteristic value extractor (first image characteristic value taking device) 102 are built up in the CPU 83 when the point image selection program 97 is activated.

The distortion correcting processor 100 processes image data of those CE images which the doctor selects by operating the operating members 25, for the sake of correcting trapezoidal distortion, called keystone correction. As described above, the objective lens 59 of the capsule endoscope 11 (see FIG. 3) forms an omniazimuth image of a viewed body site, so the CE image data is omniazimuth image data. Since the BE image is a planer image, it is necessary to expand the CE image to be a planer image so as to detect similarity or coincidence between the BE image and the CE image.

For this purpose, the distortion correcting processor 100 subjects the image data of those CE images which are selected by the doctor to a keystone correction process to produce the expanded image data. Thereby the image data of the respective points are converted to expanded image data. It is possible to produce the expanded image data by other known distortion correction method or image expansion method than the keystone correction.

Te 101 produces spectral image data of an arbitrary spectral frequency band (wavelength band) from the expanded image data that is produced by the distortion correcting processor 100. In order to detect exactly whether the probing tip 37a reaches the selected points during the endoscopy with the balloon endoscope 31, it is desirable that the point image data is definitely different from the CE image data of peripheral areas around the selected points. If the point image data of one point is similar to the CE image data of the peripheral area around that point, a mistake is likely to occur that the probing tip 37a is considered to reach the destination point before the probing tip 37a reaches that point.

To prevent such an error, the spectral image producer 101 produces spectral image data (first spectral image) from the expanded image data as produced by the distortion correcting processor 100. Thus, every point image data of the respective images selected by the doctor is converted to the expanded image data and then to the spectral image data. In the field of medical diagnosis with the endoscopy, the spectral images of the targets are often produced to facilitate finding out lesions, because the spectral images can enhance appropriate features of the targets, e.g. blood vessels or some organs such as stomach inner walls and bowel surface tissues, without the need for coloring the targets. Producing the spectral image data of the respective points to enhance some features of these points, e.g. blood vessels, is increasing the difference between the point image data and the CE image data of the periphery of the selected point. Since the spectral frequency band that is effective to increase the difference between the point image data and the peripheral CE image data varies depending upon the target organ, the spectral image producer 101 is designed to produce the spectral image data of a variable spectral frequency band, which is adjustable through the operating members 25.

When an operation for displaying a spectral image is done on the operating members 25, the spectral image producer 101 reads out coefficient matrix (not shown) from the data storage 88 or another memory location, to execute a matrix calculation for multiplying the expanded image data with coefficients of the matrix, thereby to produce the spectral image data. Since the method of producing the spectral image data using a coefficient matrix is well-known in the art and is disclosed for example in JPA 2007-319442, the description of this method is omitted here. It is possible to use another method for producing the spectral image data.

The image characteristic value extractor 102 extracts characteristic values from the spectral image data of the first to the $Z^{th}$ pass points and the spectral image data of the aimed point. Hereinafter, the spectral image data of the pass points and that of the aimed point will be referred to as the pass point spectral image data and the aimed point spectral image data. The characteristic values of the aimed point spectral image data as well as the pass point spectral image data, which correspond to the first mentioned first image characteristic values, represent numerical information on characteristic values of the individual images, including total hue, color distribution, contour distribution and shape of each image. These characteristic values are served to calculate similarity of the BE image data to the image. In the present embodiment, image characteristic values representative of patterns of blood vessels in the individual point image are extracted.

The image characteristic values representative of the blood vessel patterns may be "distribution of edge directions of blood vessels", "distribution of curvatures of blood vessels", "the number of vascular branch-off points and their relative locations" and "variation pattern in the edge directions of blood vessels". The distribution of edge directions of blood vessels means a distribution of the directions of edges (lateral or radial ends of contours) of blood vessels. Specifically, all blood vessels contained in the spectral images of the aimed point and the respective pass points, which are based on the point spectral image data, are subdivided into segments of constant lengths, and the direction of each segment of the blood vessel is detected as an angle (0° to 180°) to a reference direction that may be predetermined appropriately. Thus, the distribution of edge directions represents distribution of the directions of the respective blood vessel segments.

The distribution of curvatures represents a distribution of curvatures of the respective segments of all blood vessels contained in the spectral images of the respective points. The number of vascular branch-off points and their relative locations represent the number of branch-off points of the blood vessels in each spectral image of the selected points and the relation in location between these branch-off points. The relation in location between the branch-off points may for example be expressed in an XY coordinate system, of which a reference point (0, 0) is defined in the image at an appropriate one of the branch points. The variation pattern in the direction of vascular edges represents variation patterns of the blood vessels contained in the spectral images of the respective points. As an example of a variation pattern, a blood vessel spreads into two branches and the two branches further spreads into two and three directions respectively.

The method of extracting image characteristic values of the blood vessel pattern may be a conventional one, so the description of the blood vessel pattern extracting method is omitted here. Data of the point image characteristic values extracted by the image characteristic value extractor 102 are accompanied with additional information on spectral frequency band of the point spectral image data and on file name of image files of the respective point images as the originals of the respective point spectral images. The spectral frequency band data is obtained from the spectral image producer 101, whereas the file name data is obtained from the image data storage section 93.

The image characteristic value extractor 102 outputs the characteristic values of the respective point images, which are extracted from the point spectral image data, to the data storage 88. Then the image characteristic value storage section 96 of the data storage 88 temporarily stores the respective point image characteristic values while sorting them according to the patients (see FIG. 6).

Figure 8:
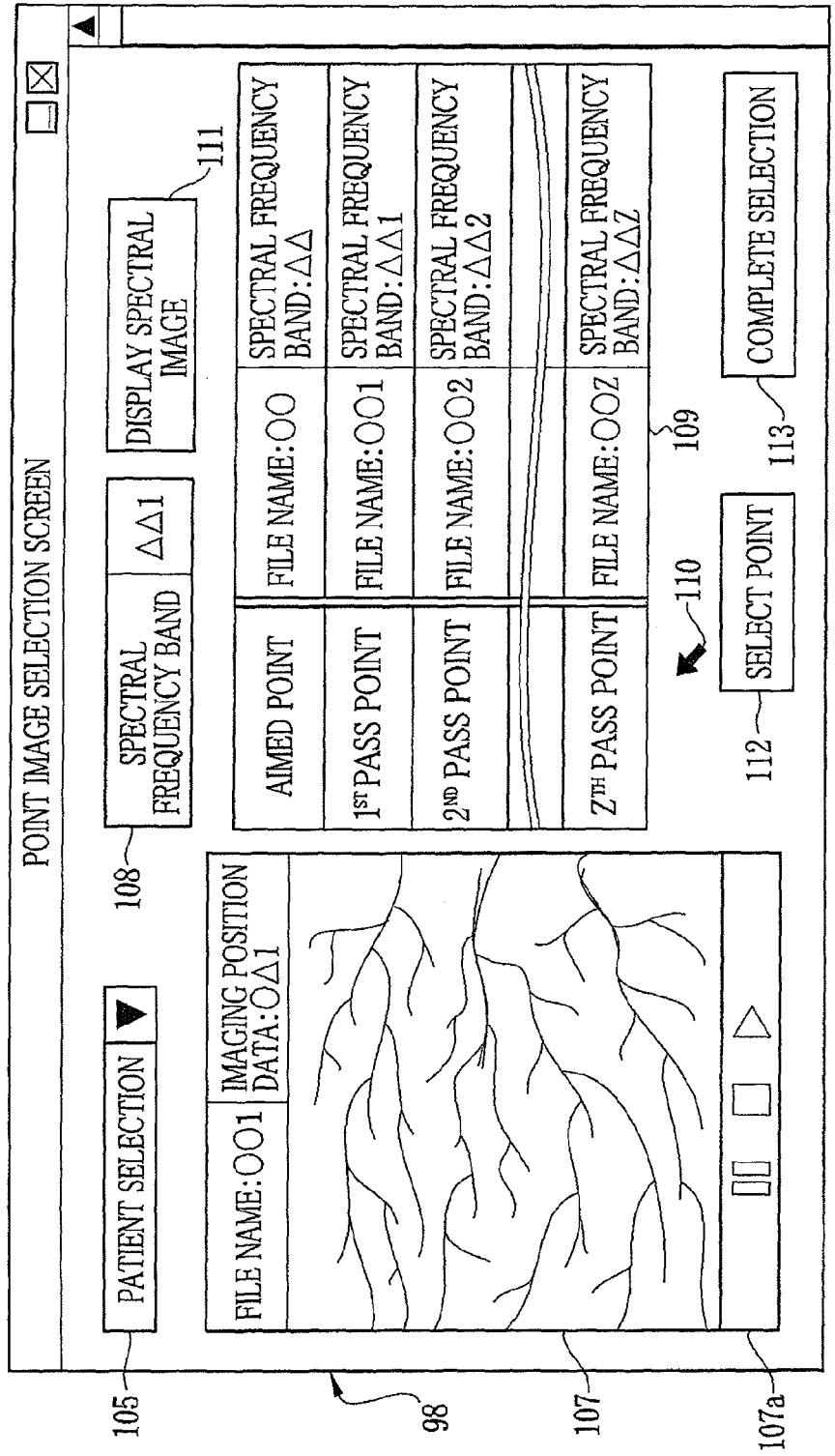
FIG. 8 is an explanatory diagram illustrating a point image selection screen for the doctor to select image files corresponding to the aimed point and the pass points.

FIG. 8 shows the point image selection screen 98, which serves for selecting the point images from the CE images that are taken through the receiver 12. The point image selection screen 98 is provided with a patient selection box 105, an image display window 107, a spectral frequency band input box 108 and a selection result display window 109.

The patient selection box 105 is used for selecting a patient 10 as a subject of an image interpretation, and the CE images obtained by the capsule endoscope 11 from the selected patient are read out from the data storage 88. When a pointer 110 is put on a mark of an inverted triangle at the right end of the patient selection box 105 and the mouse is clicked, a list of patients' names and ID numbers is displayed in the form of a pull-down menu. By clicking on one of the patients' names, the one patient is selected as the subject.

The image display window 107 displays the CE images of the patient 10 as selected in the patient selection box 105. For example, the CE images are seriatim displayed on the image display window 107 in the same order as the time sequence of imaging by the capsule endoscope 11. The doctor can control playing, pausing and quitting the display on the image display window 107 by clicking corresponding marks on a control bar 107a. Thus, the doctor interprets or investigates the CE images one by one while they are being displayed sequentially.

When the doctor does not find any portion that can be a lesion in the displayed CE image, the doctor proceeds to the next CE image without making any particular operation. If the doctor find a suspected portion that can be a lesion in the displayed CE image, the doctor pauses the display to investigate that CE image in more detail. Hereinafter the CE image containing the suspected portion will be referred to as the aimed point candidate image. With the CE image, its file name and imaging position data are displayed on an upper zone of the image display window 107. If the doctor judges it necessary to make a thorough examination of the site that is captured as the aimed point candidate image, the doctor makes an operation for producing a spectral image of the aimed point candidate image.

Specifically, the doctor inputs a spectral frequency band in the spectral frequency band input box 108, for producing the spectral image, while the aimed point candidate image is being paused on the image display window 107. Next, the doctor clicks the pointer 110 on a spectral image display button 111. Thereby, an expanded image data is produced by expanding the aimed point candidate image data, and then spectral image data having the spectral frequency band input by the doctor is produced from this expanded image data. Based on the produced spectral image data, a spectral image is displayed on the image display window 107.

When the doctor changes the spectral frequency band in the spectral frequency band input box 108 and thereafter clicks the spectral image display button 111, a spectral image having the changed spectral frequency band is displayed on the image display window 107. Thus, the doctor may repeat the same operation till a most desirable spectral image, e.g. one with an enhanced blood vessel pattern, is displayed on the image display window 107. When the desirable spectral image is displayed, the doctor clicks the pointer 110 on a point selection button 112. Then the spectral image data of the displayed spectral image is selected as the aimed point image data. Simultaneously, image characteristic values are extracted from the aimed point image data, and the extracted characteristic values of the aimed point are stored in the image characteristic value storage section 96 of the data storage 88 (see FIG. 6).

The selection result display window 109 displays file names and respective spectral frequency bands of those spectral images which are selected as the point images by the doctor. For example, when the aimed point image data is selected, a file name and a spectral frequency band of the selected image data are displayed in a raw of "aimed point" on the selection result display window 109.

After selecting the aimed point image data, the doctor selects image data of the respective pass points on the point image selection screen 98. First, those CE images are seriatim displayed on the image display window 107, which are captured from the selected patient 10 on the way from the mouth 10a or the inlet for the inserter 37 of the balloon endoscope 31 to the aimed point, in the same order as the time sequence of imaging. The doctor observes the successive CE images and pauses the display by operating the control bar 107a when such a CE image is displayed that can be the first pass point image, hereinafter referred to as the first pass point candidate image. At that time, a file name and imaging position data of the first pass point candidate image are displayed on the upper zone of the image display window 107.

The doctor checks the first pass point candidate image and its file name and imaging position data on the image display window 107, to decide whether the candidate image is to be the first pass point image or not. If the doctor does not decide the candidate image to be the first pass point image, the doctor operates the control bar 107a to restart displaying the CE images in succession. When the doctor decides on the first pass point image, the doctor inputs a spectral frequency band for the first pass point image in the spectral frequency band input box 108 and clicking the spectral image display button 111. Thereby, the CE image data of the first pass point image is expanded, and spectral image data having the designated spectral frequency band is produced from the expanded image data. Based on the spectral image data, a spectral image is displayed on the image display window 107.

The doctor repeats inputting a spectral frequency band and checking a spectral image having the input spectral frequency band on the image display window 107 till the displayed spectral image contain an enhanced blood vessel pattern that facilitates discriminating the first pass point image from others. When a desirable spectral image is displayed on the image display window 107, the doctor clicks on the point selection button 112, upon which a file name and a spectral frequency band of the selected spectral image are displayed in a raw of "first pass point" on the selection result display window 109. This means that the image data of the first pass point spectral image as displayed on the image display window 107 is selected as the first pass point image data.

Simultaneously with the selection of the first pass point image data, image characteristic values are extracted from the first pass point image data, and the extracted characteristic values of the first pass point are stored in the image characteristic value storage section 96 of the data storage 88, completing the selection of the first pass point image data.

Image files of the second and following pass point spectral images are selected in the same way as for the first pass point, and image characteristic values of the second and following pass points are stored in the image characteristic value storage section 96. When completing selecting all necessary points and their spectral images, the doctor clicks the pointer 110 on a selection complete button 113. Then the image characteristic values of the respective point images are transmitted from the image characteristic value storage section 96 to the second processor 32 through the LAN interface 90 and the LAN 29.

Now the balloon endoscope 31 and the second processor 32, which constitute the electronic endoscopy system 4, will be described in detail. As shown in FIG. 9, an optical image of a subject or target site is formed through the objective lens 41 on an imaging surface of the imaging device 42 of the balloon endoscope 31, and the imaging device 42 outputs analog picture signals from its respective pixels to an analog front end (AFE) circuit 115. The AFE circuit 115 treats the picture signals with correlated double sampling, amplification and analog-to-digital conversion, to convert them to digital BE image data. The AFE circuit 115 outputs the BE image data to the second processor 32 through the universal cord 39. It is alternatively possible to mount the AEF circuit 115 in the second processor 32 and convert the picture signals output from the imaging device 42 to the BE image data in the second processor 32.

A CPU 116 of the second processor 32 controls the overall operation of the electronic endoscopy system 4. A data bus 117 connects the CPU 116 to a RAM 119, a digital signal processor (DSP) 120, an image memory 121 and a data storage 122. The data bus 117 is also connected to an LCD driver 123 for driving the LCD 35 and a LAN interface (I/F) 124 that is connected to the LAN 29. The LAN interface 124 is supplied with the image characteristic values of the respective point images, which are fed from the first processor 24 through the LAN 29. The image characteristic values are stored in the data storage 122.

The CPU 116 reads necessary programs and data from the data storage 122 and expands them on the RAM 119 to process the read programs sequentially. The CPU 116 also controls the respective components of the second processor 32 to work in accordance with operational signals input through the operating members 34. The digital signal processor 120 processes the BE image data fed from the balloon endoscope 31. The processed BE image data is temporarily stored in the image memory 121. The image memory 121 overwrites the previously stored BE image data with the new BE image data as it is fed from the digital signal processor 120.

The LCD driver 123 is connected to a not-shown VRAM, which stores the BE image data as being read out from the image memory 121. Writing and reading of the BE image data in and out of the VRAM is being carried out in parallel to each other. The LCD driver 123 converts the BE image data, as being read out from the VRAM, to an analog composite signal for displaying the BE image on the LCD 35.

The data storage 122 has an image characteristic value storage section 126 and a program storage section 127. The image characteristic values of the respective point images, which are fed from the first processor 24, are stored in the image characteristic value storage section 126 while being sorted out them for one patient from another. Based on the image characteristic values of the respective point images, the CPU 116 detects which point the probing tip 37a has got to among the respective pass points and the aimed point while the inserter 37 of the balloon endoscope 31 is being inserted into the patient 10 for the sake of a detailed examination of the aimed point. Concretely, the CPU 116 calculates the degree of similarity between image characteristic values of the BE image data and the stored image characteristic values of the respective point images.

The program storage section 127 stores a point detection program 128 beside various programs and data for controlling the operation of the second processor 32. When the point detection program 128 is activated, a point detection screen 129 (see FIGS. 10 and 11) is displayed on the LCD 35, showing which point the probing tip 37a of the balloon endoscope 31 has reached. When the point detection program 128 is activated, a spectral image producer (second spectral image producer) 131, an image characteristic value extractor (second image characteristic value taking device) 132 and a point detector (position information obtaining device) 133 are built up in the CPU 116.

The spectral image producer 131 reads out the BE image data from the image memory 121 and produces BE spectral image data (second spectral image) from the read BE image data, so that the BE spectral image data has the same spectral frequency band as the first spectral image data of the destination point has on the basis of the image characteristic values (spectral frequency band data) of the destination point that the probing tip 37a of the balloon endoscope 31 is approaching.

For example, when the destination point is the first pass point, the spectral image producer 131 retrieves the spectral frequency band data of the first pass point image characteristic values from the image characteristic value storage section 126 of the data storage 122. On the basis of the read spectral frequency band data, the spectral image producer 131 produces the BE spectral image data having the same spectral frequency band as the first spectral image data of the first pass point has. As for the second and following pass points as well as the aimed point, the spectral image producer 131 produces BE spectral image data having the same spectral frequency band as the first spectral image data of the respective points has before the probing tip 37a reaches these points.

The BE spectral image data produced by the spectral image producer 131 is temporarily stored in a not-shown spectral image data memory location of the RAM 119. The BE spectral image data in the spectral image data memory location of the RAM 119 is revised each time a new set of BE spectral image data is written therein.

The image characteristic value extractor 132 extracts image characteristic values of the BE spectral image, hereinafter referred to as BE image characteristic values which correspond to the first-mentioned second image characteristic values, from the BE spectral image data written in the spectral image data memory location of the RAM 119. The BE image characteristic values represent image characteristic values of a blood vessel pattern in the observed site, like the above-mentioned point image characteristic values. The BE image characteristic values extracted by the image characteristic value extractor 132 is temporarily stored in a not-shown image characteristic value memory location of the RAM 119. The image characteristic value extractor 132 extracts the BE image characteristic values each time a new set of BE spectral image data is written in the RAM 119. The BE image characteristic value data in the image characteristic value memory location of the RAM 119 is revised each time a new set of BE image characteristic value data is written therein.

The point detector 133 calculates the degree of similarity between the BE image characteristic values as stored in the RAM 119 and the point image characteristic values of the destination point as stored in the image characteristic value storage section 126, which is the CE spectral image data obtained by the capsule endoscope 11 at the destination point. Based on the degree of similarity, the point detector 133 judges whether the BE spectral image data obtained by the balloon endoscope 31 is similar to the point image data of the destination point. That is, the point detector 133 judges whether the probing tip 37a of the balloon endoscope 31 reaches the destination point.

As a formula for calculating the degree of similarity, the point detector 133 uses such a function that has the larger value as the degree of similarity between two comparatives gets the higher. For example the point detector 133 uses the following formula:

$$D=C-\Sigma\{ai \times (vxi-vsi)^2\}$$

wherein vx is image characteristic values of the destination point, vs is BE image characteristic values, ai is weighting coefficient for respective parameters, and i is parameter number.

The point detector 133 compares the calculated degree of similarity with a predetermined threshold value. When the calculated degree of similarity is less than the predetermined threshold value, the point detector 133 judges that the BE image data is not similar to the point image data of the destination point, and that the probing tip 37a of the balloon endoscope 31 does not reach the destination point. If the calculated degree of similarity is equal to or more than the predetermined threshold value, the point detector 133 judges that the probing tip 37a of the balloon endoscope 31 has reached the destination point.

However, even when the balloon endoscope 31 and the capsule endoscope 11 capture images from the same point, if the images have different postures from each other at that time, the posture of the BE image differs from that of the CE image. In that case, the BE image may coincide with the CE image when the BE image rotates through an appropriate angle, e.g. 180 degrees. Without correcting the posture of the BE image, the calculated degree of similarity can be less than the predetermined threshold value, even if the probing tip 37a of the balloon endoscope 31 actually reaches the destination point. To avoid this problem, it might be possible to lower the threshold value, which increases the probability of misjudging that the probing tip 37a of the balloon endoscope 31 reaches the destination point, while the probing tip 37a does not actually reach the destination point.

To solve this problem, according to the present embodiment, a plurality of sets of rotational spectral image data are produced from the BE spectral image data while changing the posture of the image to different directions. From these different sets of rotational spectral image data, respective rotational image characteristic values are extracted. Then the point detector 133 calculates the degrees of similarity between the respective rotational image characteristic values and the point image characteristic values of the destination point as well as the BE image characteristic values and the point image characteristic values of the destination point. If at least one of these calculated degrees of similarity is equal to or more than the threshold value, the point detector 133 judges that the probing tip 37a of the balloon endoscope 31 reaches the destination point.

When it is judged that the probing tip 37a reaches the destination point, the next point is set to be the destination point. That is, when the probing tip 37a is judged to reach the first pass point, the second pass point is set to be the destination point. When the probing tip 37a is judged to reach the last pass point, the aimed point is set to be the destination point. The respective components 131 to 133 of the CPU 116 produces the BE spectral image data, extracts the BE image characteristic values, and calculates the degree of similarity on the basis of the point image characteristic values of the newly set next point. When the probing tip 37a is judged to reach the aimed point, the respective components 131 to 133 of the CPU 116 terminate the processing.

Figure 10:
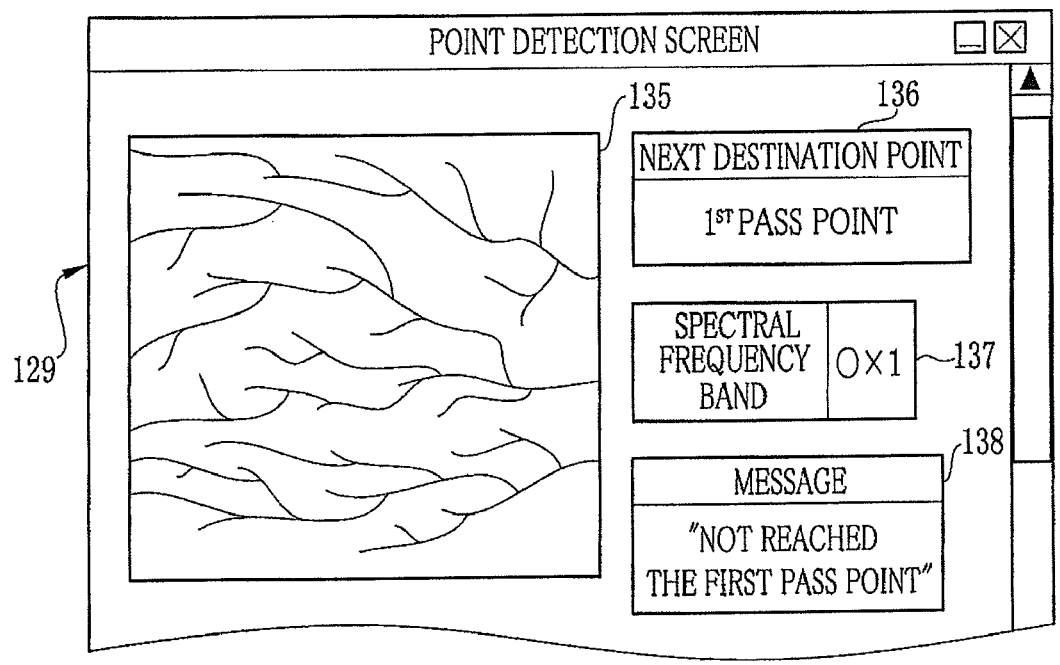
FIG. 10 is an explanatory diagram illustrating a point detection screen that shows whether the tip of the balloon endoscope has reached a destination point or not, in a stage where the tip has not yet reached the destination point.
Figure 11:
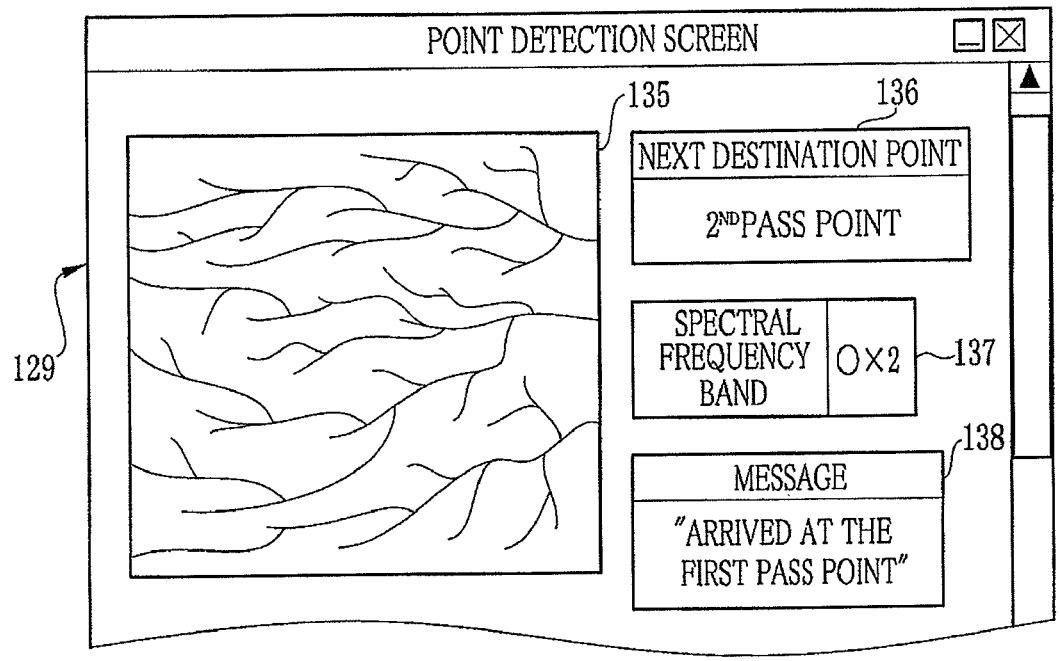
FIG. 11 is an explanatory diagram illustrating the point detection screen in a stage where the tip has reached a first pass point and a second pass point is set to be the next destination point.

As shown in FIGS. 10 and 11, the point detection screen 129 displays information on which point the probing tip 37 of the balloon endoscope 31 has reached among the first to $Z^{th}$ pass points and the aimed point. The point detection screen 129 is provided with an image display window 135, a destination point display window 136, a spectral frequency band display window 137 and a message display window 138.

The image display window 135 displays a BE image presently obtained by the balloon endoscope 31. It is possible to display a BE spectral image on the basis of the BE spectral image data, simultaneously with the BE image. The destination point display window 136 displays the name of the destination point, e.g. the first pass point. The spectral frequency band display window 137 displays information on the spectral frequency band that is attached to the data of the point image characteristic values of the destination point.

The message display window 138 displays a message that informs of whether the probing tip 37a of the balloon endoscope 31 has reached the destination point. For example, while the destination point is the first pass point and the probing tip 37a has not reached the first pass point, a message "not reached the first pass point" is displayed in the message display window 138, as shown for example in FIG. 10.

When the probing tip 37a has reached the first pass point, a message "reached the first pass point" is displayed in the message display window 138, as shown for example in FIG. 11. At that time, the second pass point is set to be a new destination point, so the destination point display window 136 displays "the second pass point", and the spectral frequency band display window 137 displays the spectral frequency band data that corresponds to the point image characteristic values of the second pass point. When the probing tip 37a has passed the first pass point, the message in the message display window 138 is revised to an appropriate one, like "not yet reached the second pass point".

In the same way as above, while the probing tip 37a of the balloon endoscope 31 is moving toward the second and following pass points and the aimed point, the name of the destination point, the spectral frequency band data on the spectral image of the destination point, and a corresponding message are displayed in the respective windows 136 to 138. So the doctor may check if the probing tip 37a of the balloon endoscope 31 gets to the destination point. If the probing tip 37a does not get to the destination point, the doctor can move the probing tip 37a forward or backward to reach the destination point. This way, the probing tip 37a of the balloon endoscope 31 finally gets to the aimed point.

Now the operation of the endoscopy system 2 as configured above will be described. In the endoscopy system 2, the patient 10 first gets an endoscopy with the capsule endoscope 11 (the capsule endoscopy system 3), and if the result of the capsule endoscopy shows any suspected portion, the patient 10 gets an endoscopy with the balloon endoscope 31 (the electronic endoscopy system 4) to investigate the suspected portion in detail.

Figure 12:
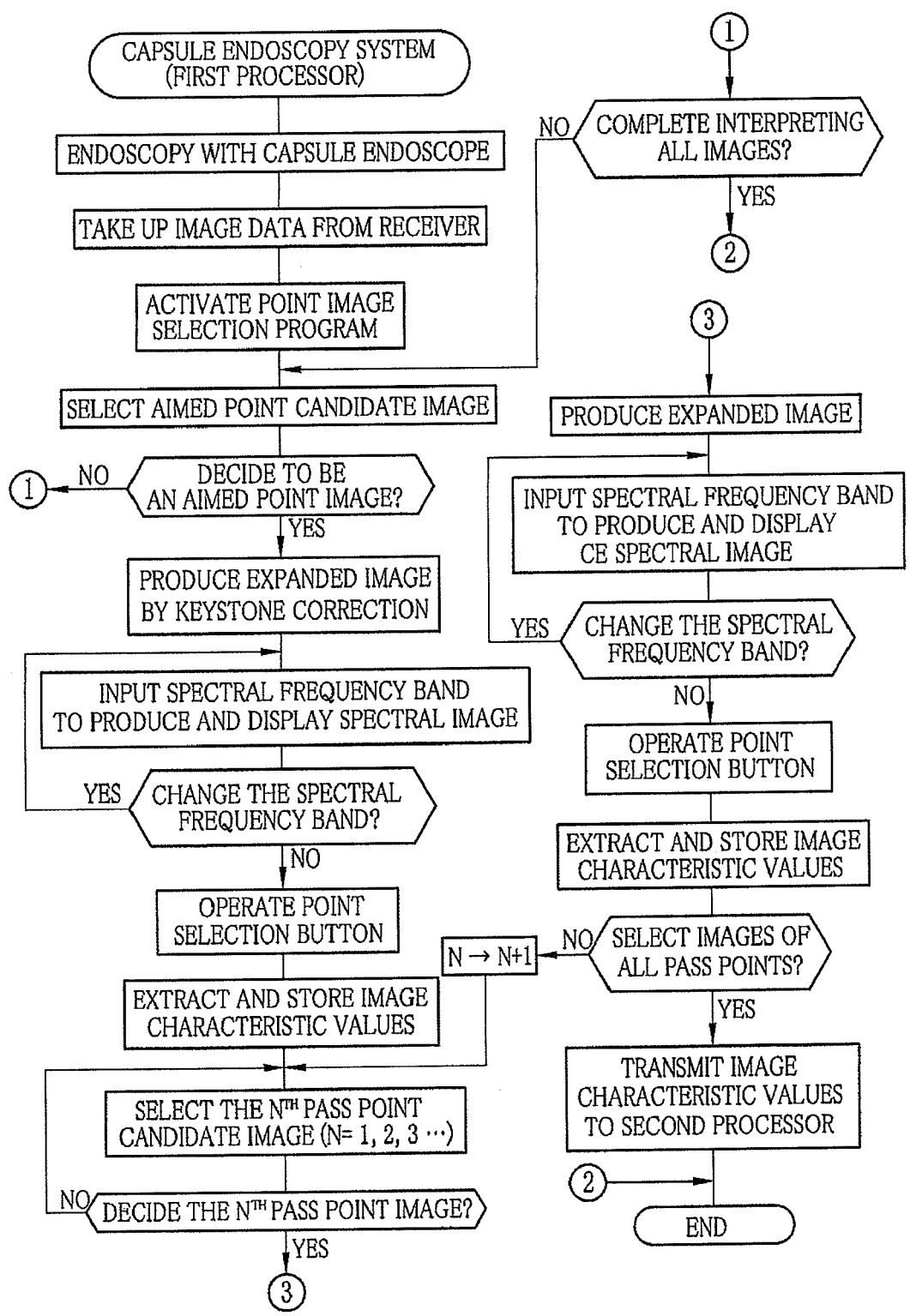
FIG. 12 is a flow chart illustrating a process of extracting image characteristic values from respective image data of an aimed point and pass points, which are selected by the doctor.

First, the procedures in the capsule endoscopy system 3 will be described with reference to FIG. 12. As a preparation for the endoscopy, the patient 10 puts the shield shirt 19 and the receiver 12 thereon. Then the patient 10 swallows the capsule endoscope 11 after its power switch being turned on. As the capsule endoscope 11 goes through the patient's tract, it captures images from internal surfaces of the tract, and sequentially transmits the CE image data of the captured images in the form of the radio wave 14. The radio wave 14 is received on the antennas 20. Simultaneously, the field strength of the received radio wave 14 is detected by the electric field strength sensor 21 that is mounted to each antenna 20. The detection results from the respective sensors 21 are input to the position detector circuit 75 of the receiver 12.

The radio wave 14 received on the antennas 20 is sent through the receiver circuit 81 to the demodulator 71, to be demodulated to the original CE image data. The CE image data is processed in the image processing circuit 72 and output to the data storage 73. The position detector circuit 75 detects the present position of the capsule endoscope 11 in the patient 10 on the basis of the detection result from the electric field strength sensor 21, and outputs the data of the present position of the capsule endoscope 11, i.e. the imaging position data, to the data storage 73. The data storage 73 stores the imaging position data in association with the image data that is fed from the image processing circuit 72.

When the imaging or endoscopy with the capsule endoscope 11 is complete, the receiver 12 is connected to the first processor 24 through the USB cable 27. Next, the doctor operates the operating members 25 to transfer the CE image data and the imaging position data from the data storage 73 to the first processor 24. Then the CE image data is stored in the image data storage section 93 of the data storage 88, and the imaging position data is stored in the imaging position data storage section 94 of the data storage 88. After the all data is transferred from the data storage 73 to the data storage 88, the doctor operates the operating members 25 to activate the point image selection program 97, thereby displaying the point image selection screen 98 on the LCD 26.

The doctor operates the pointer 110 to select the patient 10 in the patient selection box 105 on the point image selection screen 98. The CPU 83 reads out the CE image data of the selected patient from the image data storage section 93, to display the CE images of this patient successively on the image display window 107. If the displayed CE image does not contain any suspected portion that looks like a lesion, the doctor has the next CE image displayed to investigate it. If the doctor does not find any suspected portion in any of the CE images that has been transferred from the receiver 12, the doctor closes the point image selection screen 98 to terminate the point image selection process.

On the contrary, if the doctor finds such a portion that is suspected to be a lesion in the CE image displayed in the image display window 107, the doctor operates the control bar 107a to pause the displayed CE image, and investigates the displayed CE image as an aimed point candidate image. If the doctor judges it unnecessary to make a thorough examination of the suspected portion as contained in the aimed point candidate image, the doctor operates the control bar 107a to restart the successive display of the CE images. If the doctor judges it necessary to make a thorough examination of the suspected portion as contained in the aimed point candidate image with the balloon endoscope 31, the doctor operates the operating members 25 to input an appropriate spectral frequency band in the spectral frequency band input box 108 and clicks the spectral image display button 111.

Upon the spectral image display button 111 being clicked on, the distortion correcting processor 100 of the CPU 83 produces expanded image data from image data of the aimed point candidate image, and from the expanded image data, the spectral image producer 101 produces spectral image data of the input spectral frequency band that is input in the spectral frequency band input box 108. Then the CPU 83 displays a spectral image in the image display window 107 on the basis of the spectral image data produced by the spectral image producer 101.

The doctor repeats the above operation till a desirable spectral image, e.g. one having an enhanced blood vessel pattern, is displayed. When the desirable spectral image is displayed, the doctor clicks the point selection button 112. Thereby, the file name and the spectral frequency band of the selected image are displayed in the raw of "aimed point" of the selection result display window 109. Thus, the spectral image data of the aimed point is selected. Simultaneously, the image characteristic value extractor 102 extracts image characteristic values of the aimed point from the spectral image data of the aimed point, and outputs these values to the data storage 88. Then the image characteristic values of the aimed point are temporality stored in the image characteristic value storage section 96.

When the selection of the spectral image data of the aimed point is complete, the doctor begins to select pass points and spectral images of the pass points. When the doctor makes an operation for starting selecting pass point image data by the operating members 25 and the like, the CPU 83 refers to the imaging position data stored in the imaging position data storage section 94, and lets those CE images, which have been taken from the patient 10 as the capsule endoscope 11 moved from the mouth 10a to the aimed point, be displayed successively in the image display window 107. Checking the successively displayed CE images, the doctor pauses the display of such a CE image that can be a first pass point image by operating the control bar 107a.

Then the doctor checks the CE image displayed standstill in the image display window 107 and its imaging position data, to decide whether this candidate image should be selected to be a first pass point image. When the doctor decides not to select the candidate image as the first pass point image, the doctor restarts the successive display of the CE images.

When the doctor decides to select the candidate image as the first pass point image, the doctor inputs a spectral frequency band and clicks the spectral image display button 111. Then the distortion correcting processor 100 produces expanded image data from image data of the first pass point candidate image, and from the expanded image data, the spectral image producer 101 produces spectral image data of the input spectral frequency band. Then a spectral image is displayed in the image display window 107 on the basis of the spectral image data produced by the spectral image producer 101. The doctor repeats the above operation till a desirable spectral image, e.g. one having an enhanced blood vessel pattern, is displayed.

When the desirable spectral image is displayed, the doctor clicks the point selection button 112. Thereby, the file name and the spectral frequency band of the selected image are displayed in the raw of "first pass point" of the selection result display window 109. Thus, the spectral image data of the first pass point is selected. Simultaneously, the image characteristic value extractor 102 extracts image characteristic values from the spectral image data of the first pass point, and outputs these values to the data storage 88. Then the image characteristic values of the first pass point are temporarily stored in the image characteristic value storage section 96.

In the same way as for the first pass point, the second and following pass point spectral images are selected, and image characteristic values of the second and following pass points are stored in the image characteristic value storage section 96. When completing selecting all necessary points and their spectral images, the doctor clicks the selection complete button 113. Then the image characteristic values of the respective point images are transmitted from the image characteristic value storage section 96 to the second processor 32 through the LAN 29, and are stored in the image characteristic value storage section 126 of the data storage 122. At each endoscopy with the capsule endoscope 11, the above described operations and processes are carried out.

Figure 13:
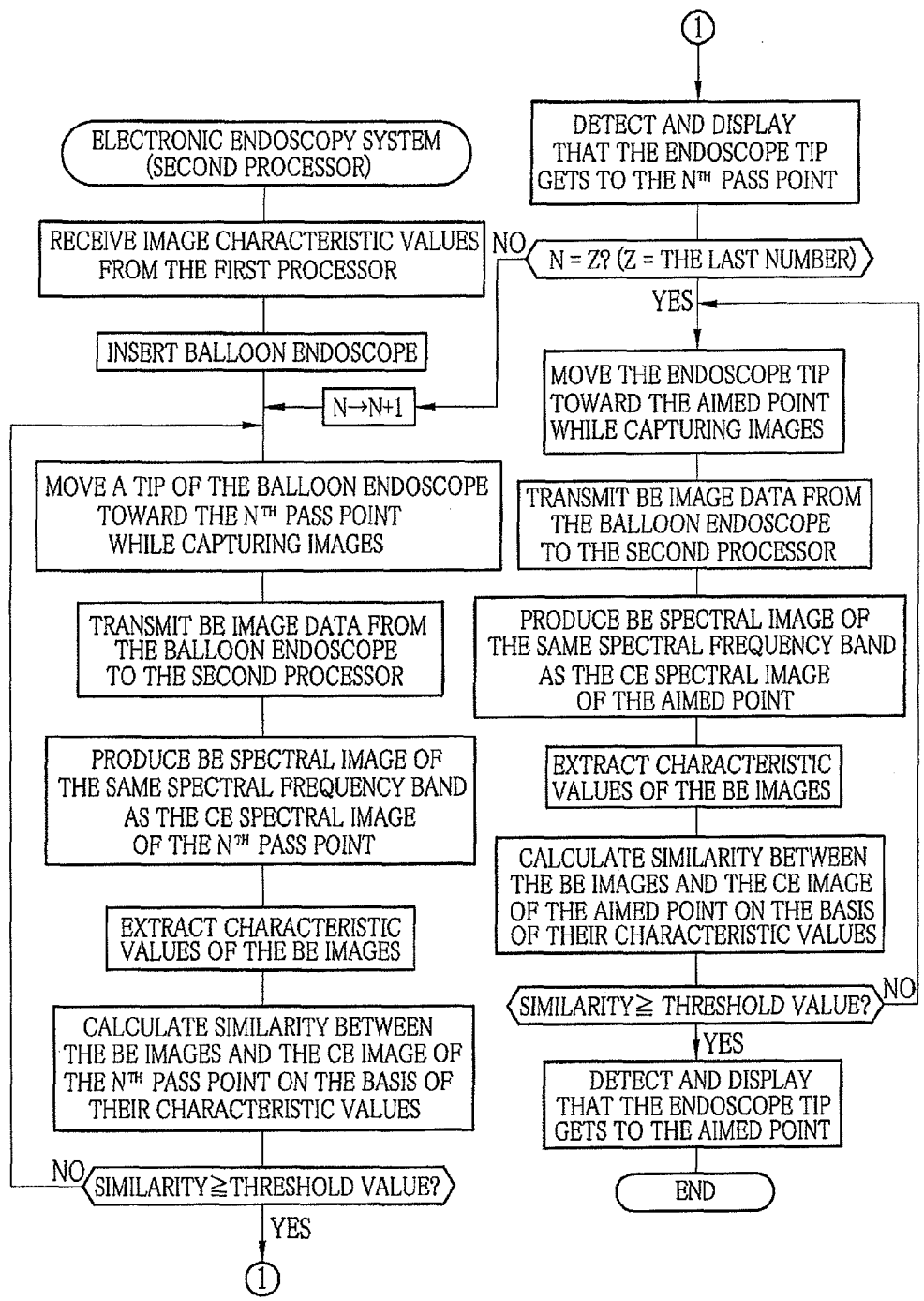
FIG. 13 is a flow chart illustrating a process of detecting which point on the endoscope insertion route the tip of the balloon endoscope has reached.

Next, the doctor makes a thorough examination of the aimed point, which is found by the endoscopy with the capsule endoscope 11. The procedure of the thorough examination using the electronic endoscopy system 4 will be described with reference to FIG. 13. First the doctor inputs information on the patient 10 as the subject of the electronic endoscopy, connects the universal cord 39 of the balloon endoscope 31 to the second processor 32 and the illuminator 33, and activates the point detection program 128 by operating the operating section 34.

When the point detection program 128 is activated, the point detection screen 129 is displayed on the LCD 35. The CPU 116 initially sets up the first pass point as the destination point, and reads out the image characteristic values of the first pass point image of the subject patient 10 from the image characteristic value storage section 126 of the data storage 122. Then the name of the next destination point, the corresponding spectral frequency band data and the message are displayed in the respective windows 136 to 138 of the point detection screen 129.

When the point detection screen 129 is displayed on the LCD 35, the doctor turns the illuminator 33 on and inserts the inserter 37 of the balloon endoscope 31 through the mouth 10a into the tract of the patient 10, so that the imaging device 42 built in the probing tip 37a captures images from internal surfaces of the tract. Analog picture signal output from the imaging device 42 is converted through the AFE circuit 115 to digital image data. The BE image data obtained this way by the balloon endoscope 31 is fed to the second processor 32 through the universal cord 39.

The BE image data is processed in the digital signal processor 120 of the second processor 32 and then stored in the image memory 121. Based on the BE image data stored in the image memory 121, the BE image is displayed in the image display window 135 of the point detection screen 129. While watching the BE image in the image display window 135, the doctor advances the probing tip 37a toward the first pass point by drawing the patients' small intestines with the balloon 48 of the balloon endoscope 31.

Simultaneously, the spectral image producer 131 of the CPU 116 produces BE spectral image data having the same spectral frequency band as the spectral image data of the first pass point has on the basis of the spectral frequency band data included in the first pass point image characteristic values, which has previously been read out from the image characteristic value storage section 126. Then the image characteristic value extractor 132 extracts the BE image characteristic values from the BE spectral image data as produced by the spectral image producer 131.

Next, the point detector 133 calculates the degree of similarity between the BE image characteristic values, which are extracted by the image characteristic value extractor 132, and the first pass point image characteristic values. If the calculated degree of similarity is less than the predetermined threshold value, the point detector 133 judges that the probing tip 37a of the BE 31 has not reached the first pass point. Then a message "not reached the first pass point" is displayed in the message display window 138, so the doctor further advancing the probing tip 37a of the balloon endoscope 31 to reach the first pass point.

When the calculated degree of similarity gets to the predetermined threshold value, the CPU 116 judges that the probing tip 37a has reached the first pass point, and a message "reached the first pass point" is displayed in the message display window 138. So the doctor can confirm that the probing tip 37a has reached the first pass point. Since the small intestines are drawn in by the balloon 48 to move the probing tip 37a to the first pass point, the relative position of the first pass point in the patient 10 can often vary between the endoscopy with the capsule endoscope 11 and the endoscopy with the balloon endoscope 31. However, according to the present embodiment, the judgment as to whether the probing tip 37a has reached the first pass point or not is done on the basis of the result of calculation about the similarity between the BE image characteristic values and the image characteristic values of the first pass point image. Therefore, regardless of the variation in relative position of the first pass point, it is possible to judge with precision that the probing tip 37a has reached the first pass point.

When the CPU 116 judges that the probing tip 37a has reached the first pass point, it sets the second pass point to be the next destination point, and reads out the image characteristic values of the second pass point image from the image characteristic value storage section 126. Then "the second pass point" is displayed as the name of the next destination point in the window 136, and the corresponding spectral frequency band data and the message are displayed in the respective windows 137 and 138. On the basis of the image characteristic values of the second pass point image, the respective components 131 to 133 of the CPU 116 produce the BE spectral image data from the BE image data obtained by the balloon endoscope 31, extract the BE image characteristic values and calculate the degree of similarity between the BE image characteristic values and the second pass point image characteristic values.

As the probing tip 37a of the balloon endoscope 31 moves to the second and following pass points and further to the aimed point, the same procedures as above: producing the BE spectral image data, extracting the BE image characteristic values and calculating the degree of similarity, are carried out on the basis of the BE image data obtained by the balloon endoscope 31 and the point image characteristic values of the next destination point. Depending upon whether the degree of similarity is more or less than the threshold value, the judgment is made as to whether the probing tip 37a gets to the destination point or not. The result of judgment is displayed on the point detection screen 129. Thus, the doctor can sequentially advance the probing tip 37a to the respective pass point and finally to the aimed point. When the probing tip 37a has reached the aimed point, the doctor accurately examines the aimed point with the balloon endoscope 31.

As described so far, in the endoscopy system 2 of the present invention, an endoscopy with the capsule endoscope 11 is first made to find an aimed point to be examined in detail with the balloon endoscope 31. Among the CE images obtained by the capsule endoscope 11, those representative of the aimed point and the pass points are selected as the point images. The balloon endoscope 31 is advanced to the aimed point while checking the similarity between each of the selected point images and the BE images obtained by the balloon endoscope 31. Thus, even though the probing tip 37a of the balloon endoscope 31 is moved through the small intestines by drawing them in with the balloon 48, it is possible to detect exactly which point in the patient's body the probing tip 37a has reached. That is, it is possible to detect the relative position of the probing tip 37a in the tract or small intestines of the patient 10.

Producing the CE spectral image data from the point images of the respective points and judging similarity between each point image and the BE image on the basis of the CE spectral image data and the BE spectral image data ensure exact detection of whether the probing tip 37a of the balloon endoscope 31 has reached the destination point. The fact that the difference between image data captured at one point and image data captured in the periphery of that point is enhanced in the spectral image data prevents the mistake of judging the probing tip 37a to have reached the destination point while the probing tip 37a is in the periphery of the destination point.

Figure 14:
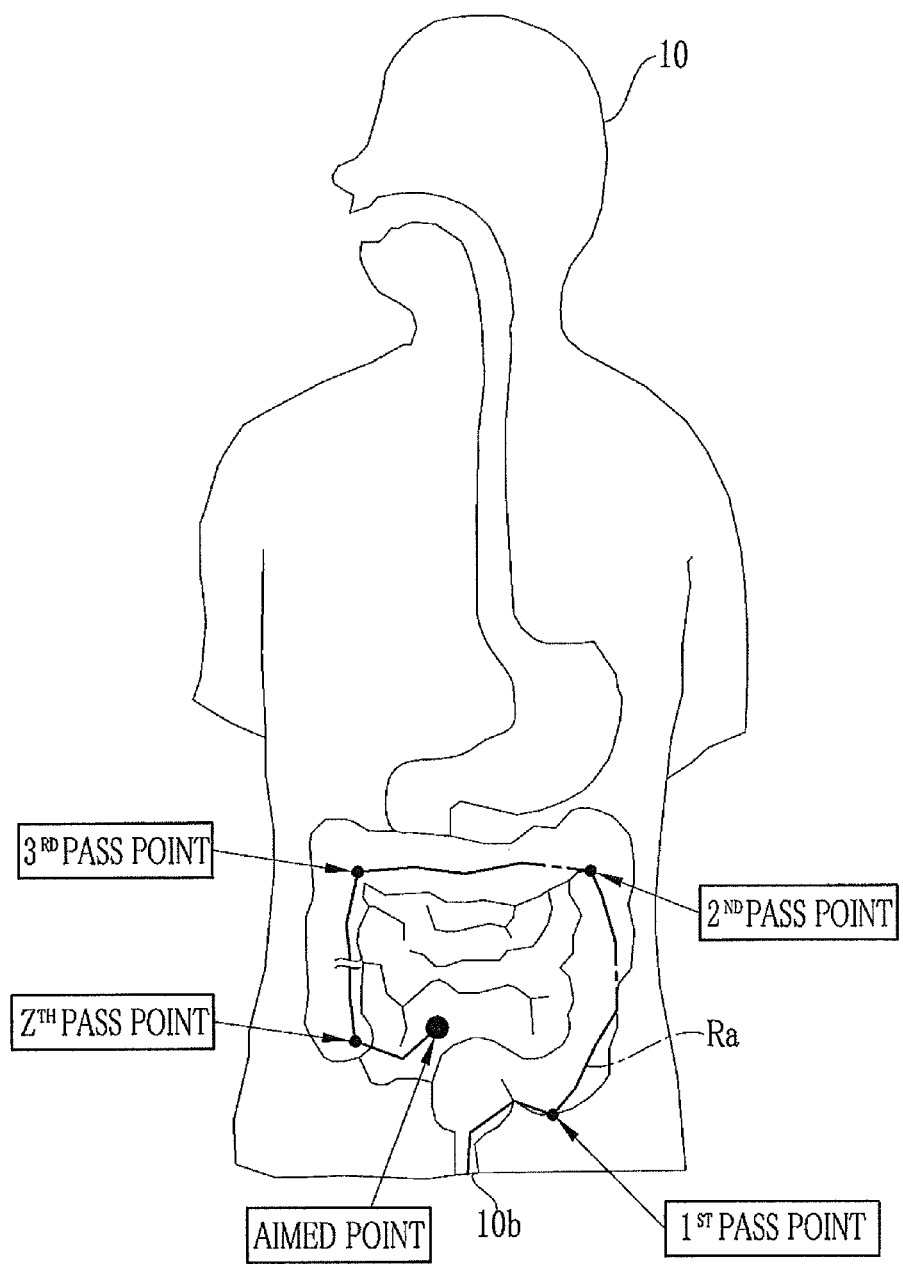
FIG. 14 is an explanatory diagram illustrating an aimed point and pass points on an endoscope insertion route from the patient's anus.
Figure 15:
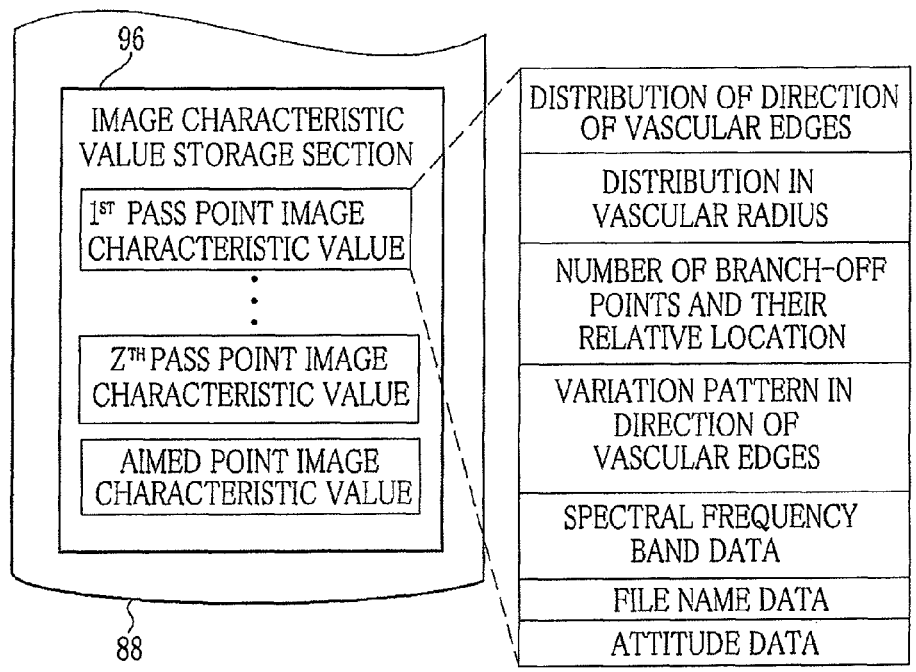
FIG. 15 is an explanatory diagram illustrating point image characteristic values used in an endoscopy system according to a second embodiment of the present invention.

Although the present invention has been described with respect to the above embodiment where the inserter 37 of the balloon endoscope 31 is inserted through the mouth 10a of the patient 10, the present invention is applicable to a case where the inserter 37 of the balloon endoscope 31 is inserted through an anus 10b of the patient 10, as shown in FIG. 14. In that case, an insertion route Ra of the balloon endoscope 31 extends from the anus 10b to the aimed point. Therefore, the first to the $Z^{th}$ pass points are selected in the order of retracing the course of the capsule endoscope 11, in opposition to the first embodiment.

In the above embodiment, "distribution of edge directions of blood vessels", "distribution of curvatures of blood vessels", "the number of vascular branch-off points and their relative locations" and "variation pattern in the edge directions of blood vessels" are referred to as the image characteristic values representative of the blood vessel patterns. But the image characteristic values are not to be limited to these factors. For example, since the branch structure of the blood vessels is a kind of fractal structure, it is possible to calculate fractal dimension values of blood vessel edges in each point image, and use the fractal dimension values as the image characteristic values. The fractal dimension value quantifies the level of complicity of a figure or structure, the vascular edges in the present case. The greater the fractal dimension value, it represents the higher complicity level of the figure. Since many methods for calculating the fractal dimension value are known, for example in JPA 2007-151608, the description thereof will be skipped.

As another method of calculating a degree of similarity between a point image and a BE image, it is possible to binarize and then thin an expanded image of the point image and the BE image to produce thinned images of the point image and the BE image, so as to calculate the degree of similarity between the thinned images, which represent core lines of the blood vessels in the present case. Note that the binarization is a process, whereby a density value for "white", e.g. "1", is assigned to those pixels having higher density values than a predetermined threshold value, while a density value for "black", e.g. "0", is assigned to those pixels having such density values that are equal to or less than the threshold value. The thinning is a process, whereby connected components of the image data are converted to linear structures. Both the binarization and the thinning are well known, see for example JPA 2007-117108 and JPA 2005-157902, the description of these process will be skipped.

In the above embodiment, the imaging position data, which represents the position of the capsule endoscope 11 inside the test body, is detected based on the result of measurement of the electric field strength of the radio wave 14 from the capsule endoscope 11. But the imaging position data may be detected other ways. For example, the capsule endoscope 11 may be provided with acceleration sensors for detecting acceleration degrees of the capsule endoscope 11 in three axial directions. Dural integration of these acceleration degrees will provide a travel distance of the capsule endoscope 11, and the imaging position data may be detected based on the travel distance.

Although the above-described embodiment produces the spectral image of a single spectral frequency band from the expanded image data of each point image, the present invention is not limited to this, but it is possible to produce two or more spectral images of different spectral frequency bands from the expanded image data of each point image. In that case, plural sets of spectral image data should be produced from each BE image, so as to have the corresponding spectral frequency bands to the point spectral images respectively. Then the similarity between the point spectral image data and the BE spectral image data of the same spectral frequency band is judged individually. Comparing the point spectral images of variable frequency bands with the BE spectral images of the corresponding frequency bands contributes to improving accuracy of detection about whether the probing tip 37a of the balloon endoscope 31 has reached the destination point or not.

On producing the plural spectral images of variable frequency bands from one CE image, it is possible to determine a set of different spectral frequency bands or wavelength bands individually for each patient or commonly to every patient. The set of different spectral frequency bands may be determined manually by the doctor or automatically according to information on the patient, such as the past illness and the suspected disease. It is possible to produce the spectral image data of different spectral frequency bands automatically in the processor or the like instead of the manual production by the doctor.

Although the doctor selects the spectral frequency band appropriately for each point to produce the point spectral image data from the expanded image data of the CE point image obtained by the capsule endoscope 11, the present invention is not to be limited to this. For example, it is possible to decide the spectral frequency band for the spectral image data according to the site or organ, e.g. stomach, small bowel or large bowel, where the point image data was obtained. This is because every organ or site mostly has such a spectral frequency band that enhances vascular pattern in that organ or site the best.

Next, an endoscopy system according to another embodiment of the present invention will be described. Since the first embodiment does not detect which portion on the internal surface of the tract, i.e. the small intestine in this case, the capsule endoscope 11 captured an image from, which is selected as a point image representative of a destination point, i.e. a pass point or aimed point, it is sometimes difficult to find the pass point or aimed point on the basis of the BE images captured by the balloon endoscope 31. For example, when the point image is an image of a front side portion of the internal wall of the small intestine, the similarity between the point image and a BE image will not be high if the balloon endoscope 31 captures the BE image from the opposite side, i.e. back side, even while the probing tip 37a gets to the destination point represented by the point image, i.e. the imaging position of the capsule endoscope 11 for that point image.

To solve this problem, according to the second embodiment, not only the relative position of the capsule endoscope 11 inside the tract but also the attitude of the capsule endoscope 11, e.g. which side of the inner wall the objective lens 59 faces to, are detected and stored as imaging position data. While the doctor advances the probing tip 37a of the balloon endoscope 31 to a destination point, information on the attitude of the capsule endoscope 11 at the imaging position for the destination point is displayed on the LCD 35.

For this purpose, as shown in FIG. 3, the attitude sensor 140 is provided in the capsule endoscope 11, to detect the attitude or orientation of the capsule endoscope 11 inside the tract of the test body. The attitude sensor 140 may be any sensor insofar as it can detect the attitude of the capsule endoscope 11. For example, the attitude sensor 140 may be a triaxial accelerometer or gravity sensor, or an attitude gyro. Since many methods of detecting the attitude of the capsule endoscope 11 with an attitude sensor are known in the art, for example from JP 3631265, JPA 2006-239053 and JPA 2006-068109, the description thereof will be omitted.

The detection result of the attitude sensor 140, i.e. the attitude data, is modulated with the CE image data into a radio wave 14 by the modulator circuit 54, and the radio wave 14 is sent from the sender circuit 63 to the antenna 18. Thus, the attitude data is wirelessly transmitted from the capsule endoscope 11 to the receiver 12. The receiver 12 stores the attitude data in the data storage 73 while associating it with the image data.

Like the first embodiment, the attitude data as well as the image data is fed to the first processor 24, and the doctor selects images of pass points and an aimed point. Then, image characteristic values of the aimed point and the respective pass points are extracted and stored in the image characteristic value storage section 96 of the data storage 88. At that time, the attitude data representative of the attitude of the capsule endoscope 11 at each point is added to the point image characteristic values of each point.

Figure 16:
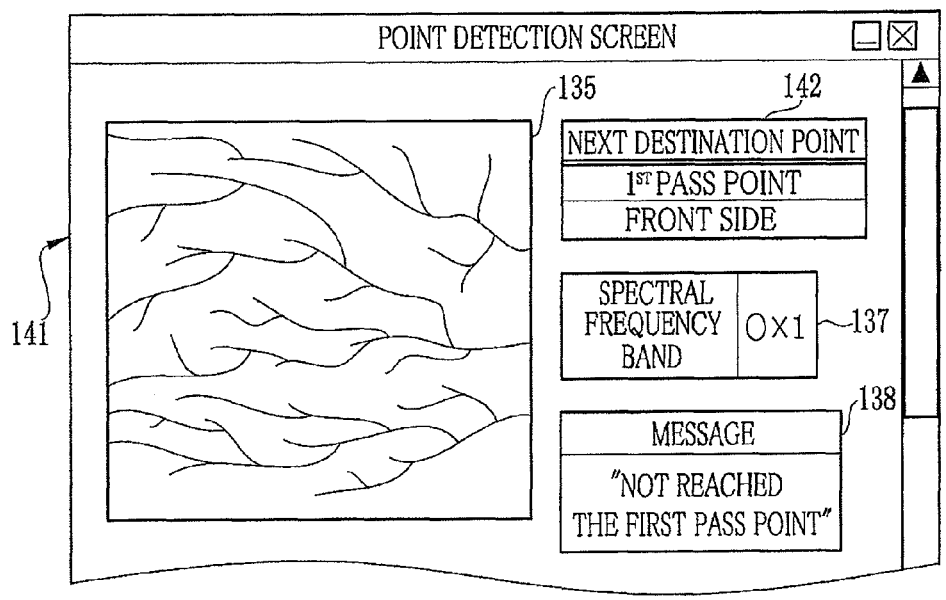
FIG. 16 is an explanatory diagram illustrating a point detection screen according to the second embodiment.

The point image characteristic values of the respective points, including the attitude data, are sent through the LAN 29 to the second processor 32, and are stored in the image characteristic value storage section 126 of the data storage 122. When the point detection program 128 is activated at the start of endoscopy with the balloon endoscope 31, a point detection screen 141 is displayed on the LCD 35, as shown in FIG. 16.

The point detection screen 141 may basically be the same as the point detection screen 129 of the first embodiment (see FIG. 10), except but the point detection screen 141 has a different destination point display window 142 from that of the first embodiment. Under the control of the CPU 116, the destination point display window 142 displays not only the name of the destination point but also information on the attitude of the capsule endoscope 11 at this destination point, on the basis of the attitude data added to the point image characteristic values of this point. For example, "front side" or "back side" or the like is displayed as the information on the attitude.

As the information on the attitude is displayed on the point detection screen 141, the doctor can see which side the destination point exists on the inner wall of the small intestine. So the doctor may focus the probing tip 37a on the side where the destination point exits, while the doctor is advancing the probing tip 37a toward the destination point. It becomes easier for the doctor to get the probing tip 37a to the destination point.

Now an endoscopy system according to a third embodiment of the present invention will be described. While the first and second embodiments extract image characteristic values representative of vascular patterns from the CE point images and the BE images, the third embodiment uses a capsule endoscope 145 and a balloon endoscope 146, which are different from the endoscopes 11 and 31 of the above embodiments, and estimates or detects information on asperities of the inner wall surface of a tract, e.g. a small intestine, from point image data and BE image data obtained by these endoscopes 145 and 146. The information on the surface asperities is used as image characteristic values.

Figure 17:
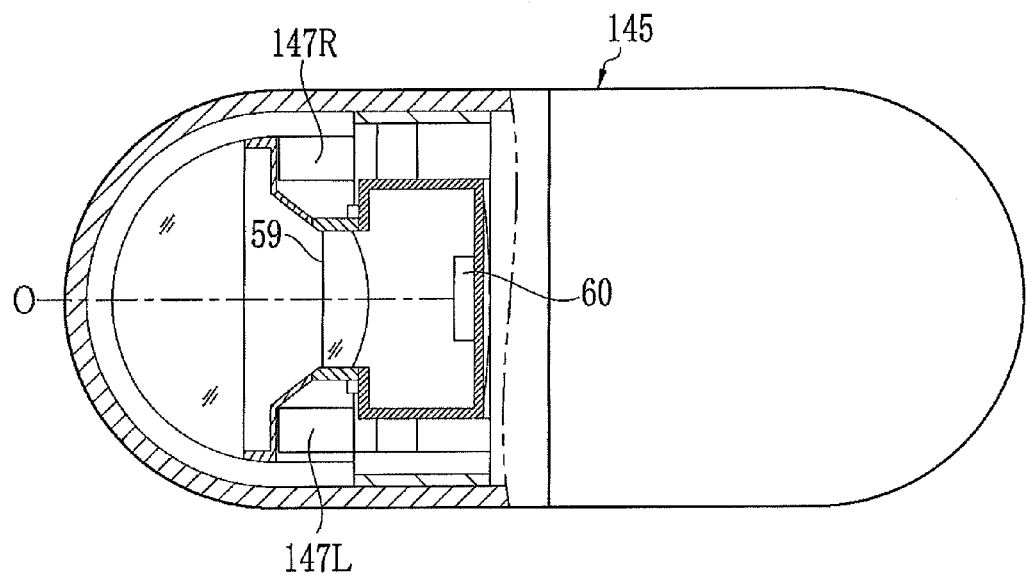
FIG. 17 is a sectional view of a capsule endoscope for use in an endoscopy system according to a third embodiment of the present invention.

As shown in FIG. 17, the capsule endoscope 145 is fundamentally configured the same way as the capsule endoscope 11, but a couple of illuminator light sources 147R and 147L are disposed symmetrically to an imaging device 60 in the capsule endoscope 145. The first and second illuminator light sources 147R and 147L are made for example of LEDs. These light sources 147R and 147R are turned on alternately to illuminate the same subject, i.e. the same body portion, and a couple of images are captured from the same subject under the light from the respective light sources 147R and 147R. The speed of switching between the light sources 147R and 147R is set so high as compared to the traveling speed of the capsule endoscope 145 through the small intestines that it is possible to capture images twice from the same subject.

As the light sources 147R and 147R alternately illuminate the bowel inner wall, asperities of the bowel inner wall cast shadows. Since the first and second light sources 147R and 147R are apart from each other, the shadows casted on the inner wall of the small intestine by the first light source 147R vary in position and size from ones casted by the second light source 147L. Accordingly, pixels of one CE image CER captured under the light from the light source 147R have different luminance values from the same pixels of the other CE image CEL have, which is captured from the same subject under the light from the second light source 147L.

Figure 18:
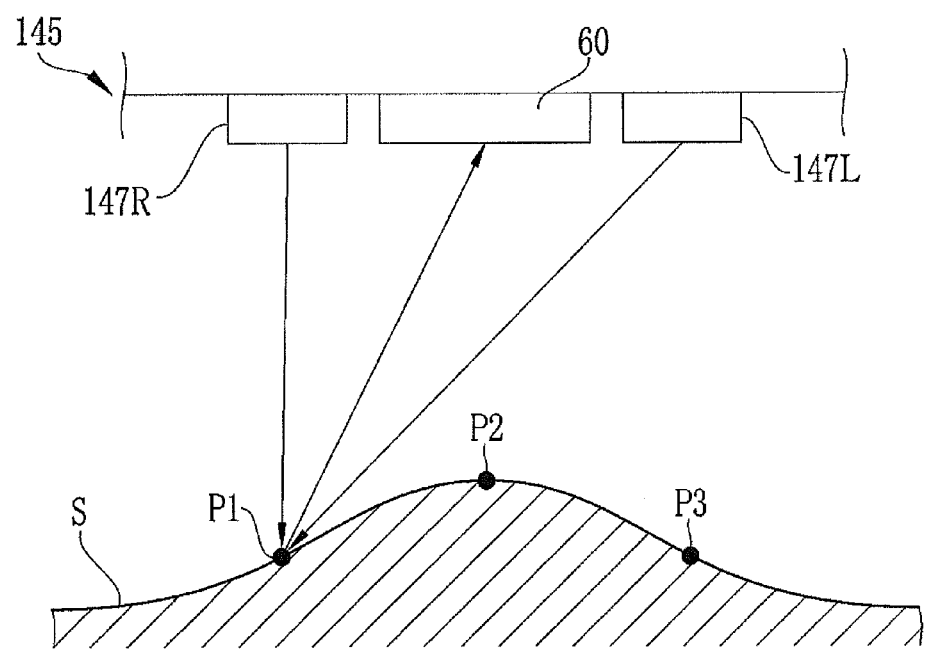
FIG. 18 is an explanatory diagram illustrating how the capsule endoscope of the third embodiment captures a couple of images from a portion while switching illumination light between a first light source and a second light source.

Assuming that the light sources 147R and 147R are substantially at the same distance from the inner wall of the small intestine, the respective luminance values of the pixels vary between the CE image CER and the CE image CEL depending upon the asperities of the inner wall of the small intestine, and more concretely the inclination of the inner wall of the small intestine. This fact will be explained with reference to an example shown in FIGS. 18 and 19, where the imaging device 60 faces a peak P2 of a convex bowel inner wall portion S, so a point P1 opposing to the first light source 147R is on one side of the peak P2, and a point P3 opposing to the second light source 147L is on the other side of the peak P2. Note that the imaging device 60 and the light sources 147R and 147R are assumed to be disposed on the same plane, to avoid complication of the drawing.

Figures 19, 20:
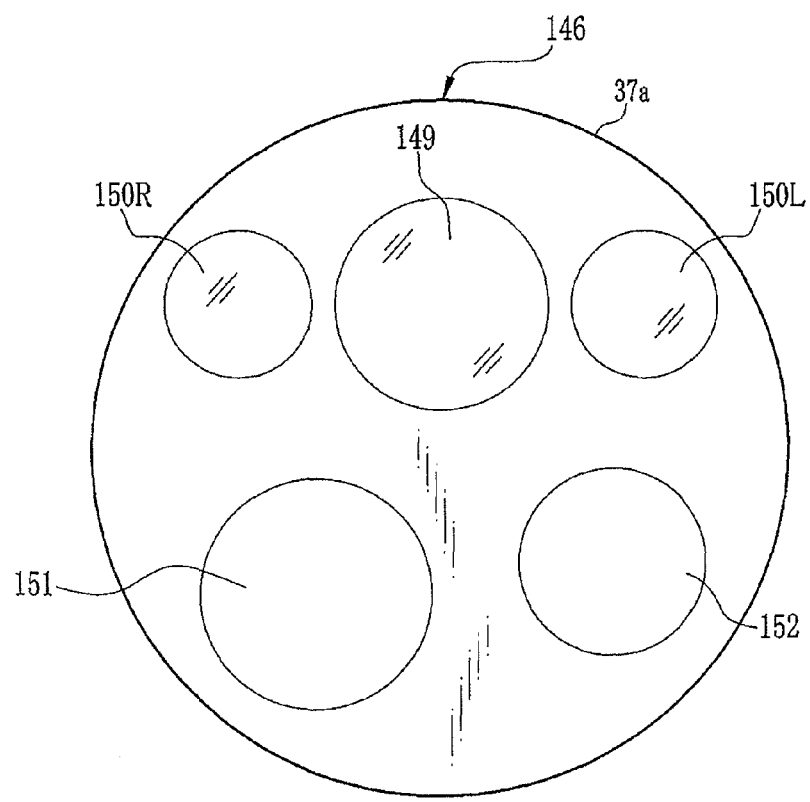
FIG. 19 is an explanatory diagram illustrating a process of estimating information on surface asperities of the subject on the basis of the couple of images captured from the same subject by the capsule endoscope of the third embodiment.
FIG. 20 is a front view of a face end of a tip of an inserter of a balloon endoscope for use in the third embodiment.

Providing that vR represents a luminance value of a pixel of the CE image CER and vL represents a luminance value of a corresponding pixel of the CE image CEL, and that D represents a difference in luminance between the counterpart pixels of the CE images CER and CEL, the difference D (=vR−vL) varies depending upon the relative positions of the respective light sources 147R and 147L to a point on the subject that corresponds to the counterpart pixels in the images CER and CEL. Specifically, since the first light source 147R has an incident angle closer to a perpendicular to the subject surface at the point P1 than the second light source 147L, the light reflected (diffusively) from the point P1 is stronger under the light from the first light source 147R. Accordingly, as shown in FIG. 19, the luminance value of the pixel corresponding to the point P1 is larger in the first CE image CER than in the second CE image CEL, so the difference D gets a positive value with respect to the point P1. Since the two light sources 147R and 147L have approximately the same incident angle at the point P2, the difference D is substantially zero. At the point P3, the second light source 147L has an incident angle closer to a perpendicular to the subject surface at the point P1 than the first light source 147R, so the difference D gets a negative value with respect to the point P3. The difference D gets the larger absolute value, the larger the inclination angle of the subject surface becomes at the point P1 or P3. On the contrary, where the subject surface of the bowel inner wall is concave, the difference D is substantially zero with respect to the point P2 that is on the bottom the concave, and the difference D gets a negative value with respect to the point P1, whereas the difference D gets a positive value with respect to the point P3.

This way, it is possible to calculate the information on the asperities of the bowel inner wall from comparison between luminance values of the counterpart pixels of CE images CER and CEL of each couple, regarding the relative positions of the first and second light sources 147R and 147L to the imaging device 60.

In the third embodiment, the balloon endoscope 146 has an observation window 149, first and second illumination windows 150R and 150L, an equipment outlet 151 and a gas/water nozzle 152 in its probing tip 37a, as shown in FIG. 20. Behind the observation window 149 are disposed an objective lens 41 and an imaging device 42, like as shown in FIG. 9. The illumination windows 150R and 150L are placed symmetrically to the observation window 149, to project illumination light from an illuminator 33 toward the bowel inner wall. The equipment outlet 151 and the gas/water nozzle 152 are well known, so the description of these members will be omitted.

The illuminator 33 is controlled by a control signal from a CPU 116 of a second processor 32, to project illumination light alternately from the first illumination window 150R and then from the second illumination window 150L, and a couple of images BER and BEL are captured from the same subject under the light from the respective illumination windows 150R and 150L. Therefore, in the same way as for the capsule endoscope 145, it is possible to calculate the information on the asperities of the bowel inner wall from comparison between luminance values of counterpart pixels of the BE images BER and BEL of each couple, regarding the relative positions of the first and second illumination windows 150R and 150L to the observation window 149.

In the third embodiment, a CPU 83 of a first processor 24 and the CPU 116 of the second processor 32 individually have a not-shown ridge information estimator in place of the image characteristic value extractor of the first embodiment. The ridge information estimator in the CPU 83 obtains point image characteristic values by calculating the ridge information from those CE images CER and CEL which the doctor selects as the point images. The ridge information estimator in the CPU 116 obtains BE image characteristic values by calculating the ridge information from the BE images BER and BEL captured by the balloon endoscope 146.

By checking the similarity between the point image characteristic values and the BE image characteristic values, it is possible to detect which point the probing tip 37a of the balloon endoscope 146 has reached during the endoscopy with the balloon endoscope 146, in the same way as described with respect to the first embodiment. It is possible to obtain image characteristic values representative of vascular patterns in addition to the ridge information.

Figure 21:
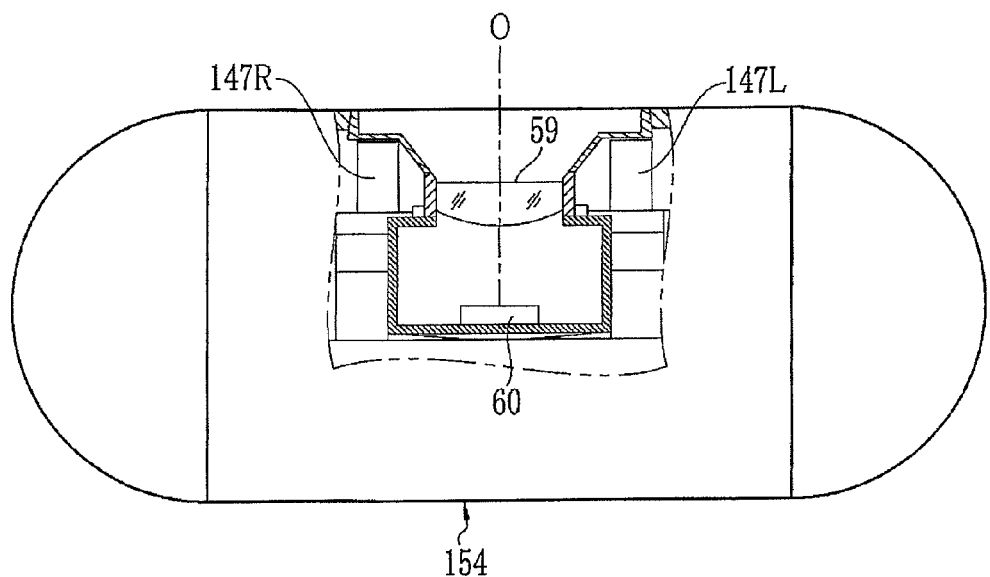
FIG. 21 is a sectional view of another capsule endoscope for use in the third embodiment.

Although an optical axis O of the objective lens 59 is oriented parallel to a longitudinal axis of the capsule endoscope 145 in the third embodiment, so that light reflected from the subject enters through a face end of the capsule endoscope 145, the present invention is not limited to this type of capsule endoscope. For example, as shown in FIG. 21, such a capsule endoscope 154 is usable that an optical axis O of an objective lens 59 is oriented perpendicular to a longitudinal axis of the capsule endoscope 154, and that light reflected from the subject enters through an observation window formed on one side of the capsule endoscope 154. Disposing first and second light sources 147R and 147L on opposite sides of an imaging device 60 symmetrically to the optical axis O in the capsule endoscope 154 enables estimating information on asperities of the bowel inner wall, in the same way as for the capsule endoscope 145.

Figure 22:
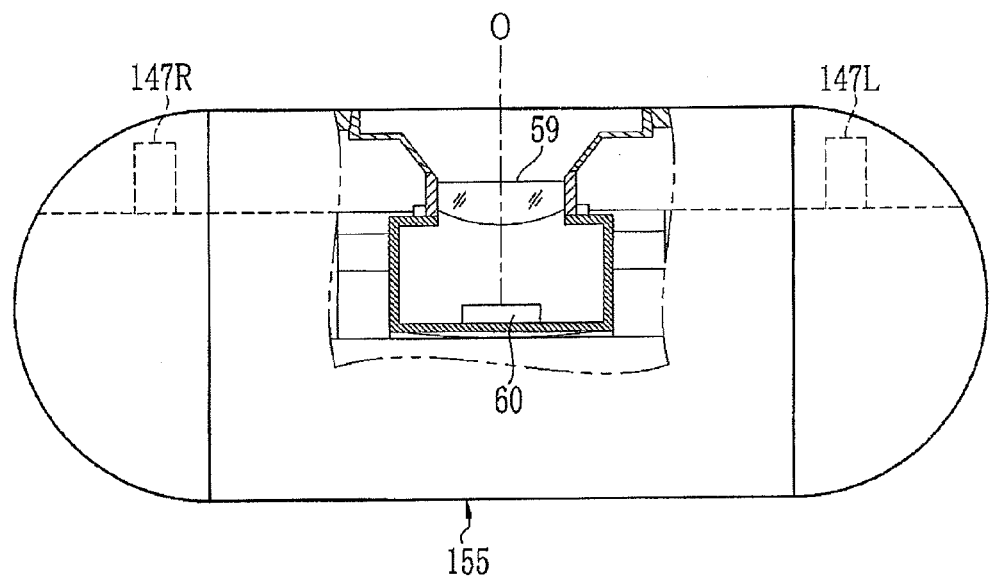
FIG. 22 is a sectional view of still another capsule endoscope for use in the third embodiment.

Although the first and second light sources 147R and 147L are disposed in the vicinity of the imaging device 60 in the capsule endoscopes 145 and 154, it is possible to dispose a pair of light sources 147R and 147L on opposite ends of a capsule endoscope 155, like as shown in FIG. 22.

Figure 23:
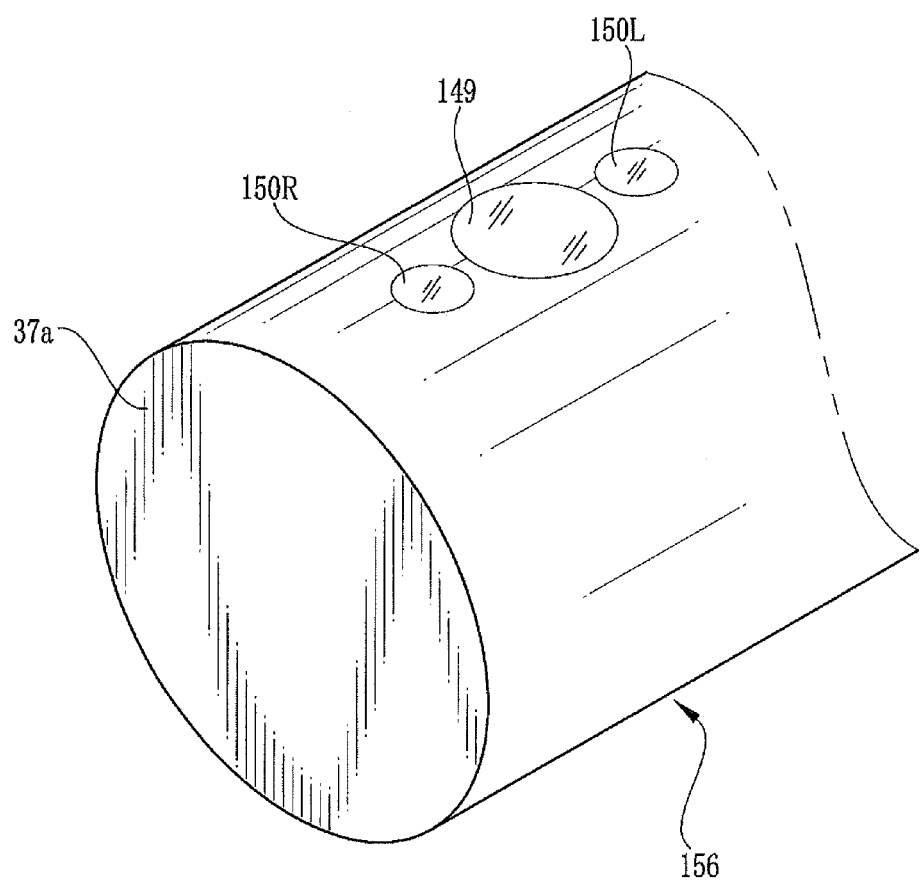
FIG. 23 is a perspective view of a tip of another balloon endoscope for use in the third embodiment.

Although the observation window 149 and the illumination windows 150R and 150L are provided on a face end of the probing tip 37a in the balloon endoscope 146 of the third embodiment, the present invention is not limited to this. For example, it is possible to provide an observation window 149 on one side of a probing tip 37a of a balloon endoscope 156, and form first and second illumination windows 150R and 150L symmetrically to the observation window 149, as shown in FIG. 23, wherein an equipment outlet and a gas/water nozzle are omitted from the drawing for clarity sake. The same object as the balloon endoscope 146 will be achieved by this configuration.

Although the above described capsule endoscopes 145, 154 and 155 have a pair of illumination light sources that are disposed symmetrically to the imaging device 60, the number and arrangement of the illumination light sources are not limited to the illustrated embodiments, but may be modified appropriately. Likewise, the number and arrangement of the illumination windows of the balloon endoscope may be modified appropriately from those of the balloon endoscopes 146 and 156. Moreover, as for the capsule endoscopes 154 and 155, it is possible to turn the imaging device 60 and the light sources 147R and 147L together. The same applies to the observation window 149 and the illumination windows 150R and 150L of the balloon endoscope 156.

In the third embodiment, surface asperities of the subject (bowel inner wall) is estimated by comparing luminance values of the counterpart pixels of the CE images CER and CEL as captured from the same portion by the capsule endoscope 145, and the information on surface asperities is used as the point image characteristic values. As another method of detecting image characteristic values of the point images, it is possible to make a calculus of difference, such as disclosed in JPA 2005-151099, for producing differential image data representative of a difference between the CE images CER and CEL of a particular point, and binarize or thin the differential image data to extract information on shadows from the binarized or thinned differential image data. The information on shadows may be used as the point image characteristic values of the particular point. In that case, information on shadows is extracted from the BE images BER and BEL of each couple, in the same way as for the CE images, to use it as BE image characteristic values.

Furthermore, it is possible to change wavelength of illumination light of the first light source 147R from that of the second light source 147L, to detect information on surface asperities of an observed site on the basis of a difference in color between the CE images CER and CEL. In this embodiment, illumination light from the first illumination window 150R also has the different wavelength from that projected from the second illumination window 150L, to detect information on surface asperities of an observed site on the basis of a difference in color between the BE images BER and BEL.

It is also possible to display the information on surface asperities or shadows of the CE image of the destination point in an enhanced manner on the BE image in an image display window 135 of a point detection screen 129 (see FIG. 10). Thereby, the doctor can visually see whether the probing tip 37a of the balloon endoscope 146 has reached the destination point or not.

Although the capsule endoscopy system 3 and the electronic endoscopy system 4 have the individual processors 24 and 32 in the above embodiment, the present invention is not limited to this configuration, but the systems 3 and 4 have a common processor. In that case, the CE image data may be transferred from the receiver 12 to the second processor 32, so that the second processor 32 manages to accept the doctor's selection of the respective point image data and extract the point image characteristic values. On the other hand, the first processor 24 has only to serve for transferring the CE image data from the receiver 12 to the second processor 32.

In the above embodiment, the similarity of the BE images obtained by the balloon endoscope 31 to the point image as selected by the doctor is judged by calculating a degree of similarity between image characteristic values of the BE image and ones of the point image. However, the present invention is not limited to this method, but it is possible to calculate directly a degree of similarity between the spectral image data of each point image and the spectral image of the BE image. In that case, the spectral image data files of the respective point images should be memorized in the second processor 32. The method of calculating the similarity between image data files can be a conventional one, so the description will be omitted.

Although the above embodiment transmits the data of the point image characteristic values from the first processor 24 to the second processor 32 through the LAN 29, the present invention is not limited to this, but the data may be transferred using various removable media.

Although the pass point images are selected by the doctor in the above embodiment, the present invention is not limited to this. For example, the CPU 83 may automatically select image data of several pass points from among those CE image data which are captured on the way from an inlet of the inserter 37 of the balloon endoscope 31, e.g. the patient's mouth, to an aimed point on the basis of the imaging position data stored in the imaging position data storage section 94, after the aimed point and its spectral image data are selected. The automatic selection of the pass point images may be done in an appropriate manner, for example, one out of a predetermined number of CE image frames (at constant intervals), or once in a predetermined length of time for capturing the CE images. From the automatically selected pass point images, the doctor may produce spectral images each individually, or a wavelength parameter or spectral frequency band may automatically be determined for the spectral image of each pass point in the way as described above.

Although the above embodiment is designed to select an aimed point image and at least a pass point image from among the CE images captured by the capsule endoscope 11, the present invention is not limited to this. For example, in a case where the aimed point is located near the inlet of the inserter 37 of the balloon endoscope 31, the doctor may have to select the aimed point image alone.

In the first embodiment, the point image selection screen 98 (see FIG. 8) is provided with the point selection button 112 for selecting the aimed point image data as well as the pass point image data, but it is possible to provide an aimed point selection button and a pass point selection button separately. Moreover, the point image selection screen 98 may be provided with a window displaying a schematic illustration of a human body like as shown in FIG. 7 that shows the selected points on the basis of the imaging position data of the selected point image data, which are stored as the imaging position data of the CE images in the imaging position data storage section 94.

Although the above embodiments refer to the balloon endoscope for small intestines as a flexible endoscope inserted in the test body, the present invention is not limited to this, but applicable to any cases using other kinds of flexible endoscopes.

Thus, the present invention is not to be limited to the above embodiment but, on the contrary, various modifications will be possible without departing from the scope of claims appended hereto.

What is claimed is:

1. An endoscopy system comprising:
a capsule endoscope swallowed by a test body to capture first kind of images from internal portions of the test body; an image processor for processing image data of the first kind of images, to display the first kind of images on a monitor for a doctor to interpret them;
a flexible endoscope having a flexible inserter with an imaging device, said flexible inserter being inserted in the test body to capture second kind of images by said imaging device when the doctor finds it necessary to make a thorough examination of an aimed point inside the test body as a result of interpretation of the first kind of images;
an aimed point selection device for selecting an aimed point image that contains said aimed point from among the first kind of images in response to an operation by the doctor;
a similarity detection device for detecting similarity between said aimed point image and the second kind of images as captured by said imaging device while said flexible inserter is being moved toward said aimed point;
a position information obtaining device for obtaining information on a relative position of said imaging device of said flexible endoscope inside the test body on the basis of the similarity detected by said similarity detection device;
a display device for displaying the information on the relative position of said imaging device;
a pass point selection device for selecting at least a pass point image from among the first kind of images, said pass point image being representative of a pass point on a route from an inlet of said flexible inserter to said aimed point, wherein said similarity detection device further detects similarity between said pass point image and the second kind of images while said flexible inserter is being inserted into the test body, and said position information obtaining device obtains the information on the relative position of said imaging device to said pass point or to said aimed point on the basis of the similarity between said pass point image and the second kind of images or the similarity between said aimed point image and the second kind of images, respectively;
a first image characteristic value taking device for taking image characteristic values respectively from said aimed point image and said pass point image; and
a second image characteristic value taking device for taking image characteristic values from the second kind of images, wherein said similarity detection device detects the similarity between said pass point image and the second kind of images by calculation using the image characteristic values of said pass point image and the second kind of image, and the similarity between said aimed point image and the second kind of images by calculation using the image characteristic values of said aimed point image and the second kind of image.

2. An endoscopy system as recited in claim 1, wherein said display device displays information as to whether said imaging device has reached said pass point or said aimed point as the information on the relative position of said imaging device.

3. An endoscopy system as recited in claim 1, further comprising:
a first spectral image producing device for producing spectral images of appropriately selected spectral frequency bands from said aimed point image and said pass point image respectively; and
a second spectral image producing device for producing a spectral image from each of the second kind of images so that said spectral image has the same spectral frequency band as said spectral image of said pass point has while said imaging device of said inserter is moving toward said pass point, and that said spectral image has the same spectral frequency band as the spectral image of said aimed point has while said imaging device of said inserter is moving from said pass point toward said aimed point, wherein said first image characteristic value taking device takes the image characteristic values from said spectral images of said aimed point and said pass point, whereas said second image characteristic value taking device takes the image characteristic values respectively from said spectral images of the second kind of images.

4. An endoscopy system as recited in claim 1, wherein the image characteristic values taken by said first and second image characteristic value taking devices represent blood vessel patterns in the internal portions of the test body.

5. An endoscopy system as recited in claim 1, wherein the image characteristic values taken by said first and second image characteristic value taking devices represent surface asperities of the internal portions of the test body.

6. An endoscopy system as recited in claim 5, wherein said capsule endoscope comprises a number of light sources, which are disposed at different positions and sequentially emit light to illuminate the same portion inside the test body, and said capsule endoscope captures a corresponding number of images to the number of said light sources from the same portion synchronously with the sequential emissions of said light sources toward the same portion, and wherein said first image characteristic value taking device estimates the surface asperities of said pass point and said aimed point on the basis of images captured from said pass point and images captured from said aimed point respectively.

7. An endoscopy system as recited in claim 6, wherein said inserter of said flexible endoscope is provided with a plurality of illumination windows on different sides of said imaging device, to project illumination light sequentially from one illumination window after another toward the same portion inside the test body, and said imaging device of said flexible endoscope captures a corresponding number of images to said illumination windows from the same portion synchronously with the sequential projection of illumination light from said illumination windows toward the same portion, and wherein said second image characteristic value taking device estimates the surface asperities of the same portion on the basis of the images captured by said imaging device of said flexible endoscope from the same portion.

8. An endoscopy system as recited in claim 1, wherein the first kind of images as captured by said capsule endoscope are omniazimuth images, and the second kind of images as captured by said flexible endoscope are planer images, and wherein said similarity detection device expands the first kind of image of said aimed point to be a planer image and compares the second kind of images with the expanded planer image of said aimed point.

9. An endoscopy system as recited in claim 1, wherein the first kind of images as captured by said capsule endoscope are omniazimuth images, and the second kind of images as captured by said flexible endoscope are planer images, and wherein said similarity detection device expands the first kind of image of said pass point to be a planer image and compares the second kind of images with the expanded planer image of said pass point.

10. An endoscopy system as recited in claim 1, wherein said capsule endoscope is provided with an attitude detector for detecting attitude of said capsule endoscope, and wherein said endoscopy system further comprises a storage device for storing information on the attitude of said capsule endoscope at said aimed point in association with said aimed point image, and said display device displays the information on the attitude of said capsule endoscope at said aimed point besides the information on the relative position of said imaging device of said flexible endoscope to said aimed point.

11. An endoscopy system as recited in claim 1, wherein said capsule endoscope is provided with an attitude detector for detecting attitude of said capsule endoscope, and wherein said endoscopy system further comprises a storage device for storing data of the attitude of said capsule endoscope at said pass point in association with said pass point image, and said display device displays the information on the attitude of said capsule endoscope at said pass point besides the information on the relative position of said imaging device of said flexible endoscope to said pass point.

12. An endoscopy method using a capsule endoscope swallowed by a test body to capture first kind of images from internal portions of the test body, and a flexible endoscope having a flexible inserter with an imaging device, said flexible inserter being inserted into the test body to capture second kind of images by said imaging device when the doctor finds it necessary to make a thorough examination of an aimed point inside the test body as a result of interpretation of the first kind of images, said endoscopy method comprising steps of:
selecting an aimed point image that contains said aimed point from among the first kind of images;

detecting similarity between said aimed point image and the second kind of images as captured by said imaging device while said flexible inserter is being moved toward said aimed point;
obtaining information on a relative position of said imaging device of said flexible endoscope inside the test body on the basis of the similarity between said aimed point image and the second kind of images;
displaying the obtained information on the relative position of said imaging device;
selecting at least a pass point image from among the first kind of images, said pass point image being representative of a pass point on a route from an inlet of said flexible inserter to said aimed point, wherein said similarity detection device further detects similarity between said pass point image and the second kind of images while said flexible inserter is being inserted into the test body, and said position information obtaining device obtains the information on the relative position of said imaging device to said pass point or to said aimed point on the basis of the similarity between said pass point image and the second kind of images or the similarity between said aimed point image and the second kind of images, respectively;
taking first image characteristic values respectively from said aimed point image and said pass point image; and
taking second image characteristic values from the second kind of images, wherein said similarity detection device detects the similarity between said pass point image and the second kind of images by calculation using the image characteristic values of said pass point image and the second kind of image, and the similarity between said aimed point image and the second kind of images by calculation using the image characteristic values of said aimed point image and the second kind of image.

* * * * *